US007078039B2

(12) United States Patent
Haynes et al.

(10) Patent No.: US 7,078,039 B2
(45) Date of Patent: *Jul. 18, 2006

(54) IMMUNOGENIC COMPOSITION

(75) Inventors: Barton F. Haynes, Durham, NC (US);
Hua-Xin Liao, Chapel Hill, NC (US);
Norman Letvin, Newton, MA (US)

(73) Assignees: Duke University, Durham, NC (US);
Beth Israel Deaconess Medical Center, Boston, MA (US)

( * ) Notice: Subject to any disclaimer, the term of this patent is extended or adjusted under 35 U.S.C. 154(b) by 52 days.

This patent is subject to a terminal disclaimer.

(21) Appl. No.: 10/973,475

(22) Filed: Oct. 27, 2004

(65) Prior Publication Data

US 2005/0112136 A1    May 26, 2005

Related U.S. Application Data

(60) Division of application No. 09/775,805, filed on Feb. 5, 2001, now Pat. No. 6,982,086, which is a continuation-in-part of application No. 09/497,497, filed on Feb. 4, 2000, now abandoned.

(51) Int. Cl.
*A61K 39/00* (2006.01)

(52) U.S. Cl. .................... 424/192.1; 424/188.1; 424/208.1; 514/2; 530/324; 530/300

(58) Field of Classification Search ............ 514/2; 424/188.1, 192.1, 208.1; 530/300, 324
See application file for complete search history.

(56) References Cited

U.S. PATENT DOCUMENTS

| | | | |
|---|---|---|---|
| 5,013,548 A | 5/1991 | Haynes et al. |
| 5,019,387 A | 5/1991 | Haynes et al. |
| 5,030,449 A | 7/1991 | Berzofsky et al. |
| 5,081,226 A | 1/1992 | Berzofsky et al. |
| 5,336,758 A | 8/1994 | Berzofsky et al. |
| 5,352,576 A | 10/1994 | Haynes et al. |
| 5,516,632 A | 5/1996 | Palker et al. |
| 5,622,703 A | 4/1997 | Berzofsky et al. |
| 5,695,762 A | 12/1997 | Berzofsky et al. |
| 5,711,947 A | 1/1998 | Berzofsky et al. |
| 5,820,865 A | 10/1998 | Berzofsky et al. |
| 5,853,978 A | 12/1998 | Berman |
| 5,864,027 A | 1/1999 | Berman |
| 5,882,853 A | 3/1999 | Berzofsky et al. |
| 5,932,218 A | 8/1999 | Berzofsky et al. |
| 5,939,074 A | 8/1999 | Berzofsky et al. |
| 5,976,541 A | 11/1999 | Berzofsky et al. |
| 5,976,551 A | 11/1999 | Mottez et al. |
| 5,980,899 A | 11/1999 | Berzofsky et al. |
| 5,993,819 A | 11/1999 | Haynes et al. |
| 5,997,869 A | 12/1999 | Goletz et al. |
| 6,042,836 A | 3/2000 | Berman et al. |
| 6,214,347 B1 | 4/2001 | Berzofsky et al. |
| 6,290,963 B1 | 9/2001 | Fischinger et al. |
| 6,294,322 B1 | 9/2001 | Berzofsky et al. |
| 6,458,527 B1 | 10/2002 | Luciw et al. |
| 6,592,872 B1 | 7/2003 | Klimpel et al. |
| 6,656,471 B1 | 12/2003 | Sastry et al. |
| 2001/0036461 A1 | 11/2001 | Haynes et al. |
| 2002/0086283 A1 | 7/2002 | Haynes et al. |
| 2003/0147888 A1 | 8/2003 | Haynes et al. |
| 2004/0001851 A1 | 1/2004 | Haynes et al. |
| 2004/0039172 A1 | 2/2004 | Haynes et al. |
| 2004/0086506 A1 | 5/2004 | Haynes et al. |
| 2004/0132010 A1 | 7/2004 | Haynes et al. |
| 2004/0197344 A1 | 10/2004 | Haynes et al. |

FOREIGN PATENT DOCUMENTS

| | | |
|---|---|---|
| EP | 0 693 938 B1 | 1/1996 |
| WO | WO 91/04051 | 4/1991 |
| WO | WO 93/04697 | 3/1993 |
| WO | WO 93/15750 | 8/1993 |
| WO | WO 94/26785 | 11/1994 |
| WO | WO 94/28929 | 12/1994 |
| WO | WO 94/29339 | 12/1994 |
| WO | WO 95/29700 | 11/1995 |
| WO | WO 96/41189 | 12/1996 |
| WO | WO 97/14436 | 4/1997 |
| WO | WO 98/01564 | 1/1998 |
| WO | WO 00/52040 | 9/2000 |
| WO | WO 01/43693 | 6/2001 |
| WO | WO 01/54719 | 8/2001 |
| WO | WO 01/56355 | 8/2001 |
| WO | WO 02/08716 | 1/2002 |
| WO | WO 02/20555 | 3/2002 |
| WO | WO 02/024149 | 3/2002 |
| WO | WO 2002/20554 | 3/2002 |
| WO | WO 02/069691 | 9/2002 |
| WO | WO 03/039470 | 5/2003 |
| WO | WO 03/046137 | 6/2003 |
| WO | WO 2004/009785 | 1/2004 |
| WO | WO 2004/075850 | 9/2004 |
| WO | WO 2005/016952 | 2/2005 |
| WO | WO 2005/028625 | 3/2005 |

OTHER PUBLICATIONS

Sheppard et al, "The characterization of non-progress: long-term HIV-1 infection will stable CD4+ T-cell levels", AIDS 7:1159-1166 (1993).

Phair, John P., Keynote Address: "Variations in the Natural History of HIV Infection", AIDS Research and Human Retroviruses 10(8):883 885 (1994).

Pantaleo et al, "Studies in Subjects with Long-Term Nonprogressive Human Immunodeficiency Virus Infection", N. Engl. J. Med. 332(4):209-216 (1995).

Cao et al, "Virologic and Immunologic Characterization of Long-Term Survivors of Human Immunodeficiency Virus Type 1 Infection", N. Engl. J. Med. 332(4):201-208 (1995).

(Continued)

*Primary Examiner*—Jeffrey Stucker
(74) *Attorney, Agent, or Firm*—Nixon & Vanderhye P.C.

(57) ABSTRACT

The present invention relates, in general, to human immunodeficiency virus (HIV) and, in particular, to an HLA-based HIV vaccine.

5 Claims, 2 Drawing Sheets

OTHER PUBLICATIONS

Pantaleo et al, "Major expansion of CD8+ T cells with a predominant Vβ usage during the primary Immune response to HIV", Nature 3970:463-467 (1994).

Mellors et al, "Quantitation of HIV-1 RNA in Plasma Predicts Outcome after Seroconversion", Ann. Intern. Med. 122:573-579 (1995).

Jurriaans et al, "The Natural History of HIV-1 Infection: Virus Load and Virus Phenotype Independent Determinants of Clinical Course?", Virology 204:223-233 (1994).

Borrow et al, "Virus-Specific CD8+ Cytotoxic T-Lymphocyte Activity Associated with Control of Viremia in Primary Human Immunodeficiency Virus Type 1 Infection", Journal of Virology 68(9):6103-6110 (1994).

Haynes et al, "Toward an Understanding of the Correlates of Protective Immunity to HIV Infection", Science 271:324-328 (1996).

Haynes, Barton F., "Scientific and Social Issues of Human Immunodeficiency Virus Vaccine Development", Science 260:1279-1286 (1993).

Nowak et al, "Antigenic Oscillations and shifting Immunodominance in HIV-1 Infections", Nature 375:606-611 (1995).

Walker et al, "CD8+ Lymphocytes Can Control HIV Infection in Vitro by Suppressing Virus Replication", Science 234:1563-1566 (1986).

Baler et al, "HIV suppression by interleukin-16", Nature 378:563 (1995).

Cocchi et al, "Identification of RANTES, MIP-1α, and MIP-1β as the Major HIV-Suppressive Factors Produced by CD8+ T Cells", Science 270:1811-1815 (1995).

Feng et al, "HIV-1 Entry Cofactor" Functional cDNA Cloning of a Seven-Transmembrane, G Protein-Coupled Receptor" Science 272:872-877 (1996).

Wei et al, "Viral dynamics in human immunodeficiency virus type 1 infection", 373:117-122 (1995).

Palker et al, "Polyvalent Human Immunodeficiency Virus Synthetic Immunogen Comprised of Envelope gp120 T Helper Cell Sites and B Cell Neutralization Epitopes", The Journal of Immunology 142:3612-3619 (1989).

Berzofsky, Jay A., "Development of artificial vaccines against HIV using defined epitopes", The FASEB Journal 5:2412-2418 (1991).

Haynes et al, "HIV Type 1 V3 Region Primer-Induced Antibody Suppression Is Overcome by Administration of C4-V3 Peptides as a Polyvalent Immunogen", AIDS Research and Human Retroviruses 11(2):211-221 (1995).

Williams and McAuley, "HLA Class I Variation Controlled for Genetic Admixture in the Gila River Indian Community of Arizona: A Model for the Paleo-Indians", Human Immunology 33:39-46 (1992).

Hardy, G.H., "Mendelian Proportions in a Mixed Population", Science, N.S. XXVIII, (706):49-50 (1908).

Schneider et al, "Enhanced immunogenicity for CD8+ T cell induction and complete protective efficacy of malaria DNA vaccination by boosting with modified vaccinia virus Ankara", Nature Medicine 4:397-402 (1998).

Ferrari et al, "Clade B-based HIV-1 vaccines elicit cross-clade cytotoxic T lymphocyte reactivities in uninfected volunteers", Proc. Natl. Acad. Sci. USA 94:1396-1401 (1997).

Cease and Berzofsky, "Toward A Vaccine For AIDS: The Emergence of Immunobiology-Based Vaccine Development", Annu. Rev. Immunol. 12:923-989 (1994).

Guleria et al, "Auxotrophic vaccines for tuberculosis", Nature Medicine 2(3):334-337 (1996).

Beddows et al, "Neutralization of primary and T-cell line adapted isolates of human immunodeficiency virus type 1: role of V3-specific antibodies", Journal of General Virology 79:77-82 (1998).

Sullivan et al, "Replicative Function and Neutralization Sensitivity of Envelope Glycoproteins from Primary and T-Cell Line-Passaged Human Immunodeficiency Virus Type 1 Isolates", Journal of Virology 69(7):4413-4422 (1995).

Rowland-Jones et al, HIV-Specific Cytotoxic T-Cells in HIV-Exposed but Uninfected Gambian Women, Nat. Med. 1(1):59-64 (1995) (Abstract).

Lee et al, "Circulating HIV-1-Infected Cell Burden From Seroconversion to AIDS: Importance of Postseroconversion Viral Load on Disease Course", Journal of Acquired Immune Deficiency Syndromes 7:381-388 (1994).

Rowland-Jones et al, "HIV-specific cytotoxic T-cells in HIV-exposed but uninfected Gambian women", Nature Medicine 1(1):59-64 (1995).

Wain-Hobson et al, Simon in the Evolutionary biology of viruses, Stephen S. Morse (ed), Raven Press, NY, pp. 185-209 (1994)—Abstract.

Ho et al, "Rapid turnover of plasma virions and CD4 lymphocytes in HIV-1 infection", Nature 373:123-126 (1995).

Robertson et al, "Recombination in AIDS Viruses", Journal of Molecular Evolution 40:249-259 (1995).

Haynes et al, "Use of Synthetic Peptides in Primates to Induce High-Titered Neutralizing Antibodies and MHC Class I-Restricted Cytotoxic T Cells Against Acquired Immunodeficiency Syndrome Retroviruses: An HLA-Based Vaccine Strategy", Transactions of the Association of American Physicians 106:33-41 (1993).

Ward et al, "Analysis of HLA Frequencies in Population Cohorts for Design of HLA-Based HIV Vaccinces", HIV Molecular Database, pp. IV-10-IV-16 (1995).

Mayr et al, "The Smallpox Vaccination Strain MVA: Marker, Genetic Structure, Experience Gained with the Parental Vaccination and Behavior in Organisms with a Debilitated Defence Mechanism", Zbl. Bakt. Hyg. I. Abt. Orig. B 167:375-390 (1978).

Barlett et al, "Safety and immunogenicity of an HLA-based HIV envelope polyvalent synthetic peptide immunogen", AIDS 12:1291-1300 (1998).

Haynes et al, "HIV Type 1 V3 Region Primer-Induced Antibody Suppression Is Overcome by Administration of C4-V3-Peptides as a Polyvalent Immunogen", AIDS Research and Human Retroviruses 11(2):211-221 (1995).

Clerici, et al., "Detection of Cytotoxic T Lymphocytes Specific for Synthetic Peptides of gp 160 in HIV-Seropositive Individuals", The Journal of Immunology, vol. 146, No. 7, pp. 2214-2219 (1991).

Hart, et al., "Priming of an Anti-Human Immunodeficiency Virus (HIV) CD8+ Cytotoxic T Cells In Vivo by Carrier-Free HIV Synthetic Peptides", Proc. Natl. Acad. Sci. USA, vol. 88, pp. 9448-9452 (1991).

Haynes, et al., "Conversion of an Immunogenic Human Immunodeficiency Virus (HIV) Envelope Synthetic Peptide to a Tolerogen in Chimpanzees by the Fusogenic Domain of HIV gp41 Envelope Protein", The Journal of Experimental Medicince, vol. 177, pp. 717-727 (1993).

Haynes, et al.,"Induction of HIVMN Neutralizing Antibodies in Primates Using a Prime-Boost Regimen of Hybrid Synthetic gp120 Envelope Peptides", The Journal of Immunology, vol. 151, No. 3, pp. 1646-1653 (1993).

Hosmalin, et al., "Priming with T Helper Cell Epitope Enhances the Antibody Response to the Envelope Glycoprotein of HIV-1 in Primates", The Journal of Immunology, vol. 146, No. 5, pp. 1667-1673 (1991).

Liao, et al., "Increased Immunogenicity of HIV Envelope Subunit Complexed with $\alpha_2$-Macroglobulin When Combined with Monophosphoryl Lipid A and GM-CSF", Vaccine, vol. 20, pp. 2396-2403 (2002).

Shirai, et al., "Broad Recognition of Cytotoxic T Cell Epitopes from the HIV-1 Envelope Protein with Multiple Class I Histocompatibility Molecules", The Journal of Immunology, vol. 148, No. 6, pp. 1657-1667 (1992).

Wain-Hobson, "Is Antigenic Variation of HIV Important for AIDS and What Might Be Expected in the Future?", The Evolutionary Biology of Viruses. Stephen S. Morse (ed), Raven Press, Ltd., New York, pp. 185-209 (1994).

Riffkin et al, "A single amino-acid change between the antigenically different extracellular serine proteases V2 and B2 from *Dichelobacter nodosus*", Gene 167:279-283 (1995).

Abaza et al, "Effects of amino acid substitutions outside an antigenic site on protein binding to monoclonal antibodies of predetermined specificity obtained by peptide immunization", Journal of Protein Chemistry 11(5):433-444 (1992).
Cruse et al, Illustrated Dictionary of Immunology (Boca Raton, FL, CRC Press, Inc., p. 309, QR180.4.C78 (1995).
Paul, Fundamental Immunology (Philadelphia & New York, Lippincott-Raven Publishers, pp. 250, 1311, 1312 QR181. F84 (1993).
Ahlers, et al., "Construction of an HIV-1 Peptide Vaccine Containing a Multideterminant Helper Peptide Linked to a V3 Loop Peptide 18 Inducing Strong Neutralizing Antibody Responses in Mice of Multiple MHC Haplotypes After Two Immunizations", The Journal of Immunology, vol. 150, No. 12, pp. 5647-5665 (1993).
Ahlers, et al., "Candidate HIV Type 1 Multideterminant Cluster Peptide-P18MN Vaccine Constructs Elicit Type 1 Helper T Cells, Cytotoxic T Cells, and Neutralizing Antibody, All Using the Same Adjuvant Immunization", AIDS Research and Human Retroviruses, vol. 12, No. 4, pp. 259-272 (1996).
Berzofsky, et al., "Antigenic Peptides Recognized by T lymphocytes from AIDS Viral Envelope-Immune Humans", Nature, vol. 334, pp. 706-708 (1988).
Novitsky et al, "Identification of Human Immunodeficiency Virus Type 1 Subtype C Gag-, Tat-, Rev-, and Nef-Specific Elispot-Based Cytotoxic T-Lymphocyte Responses for AIDS Vaccine Design", Journal of Virology 75(19):9210-9228 (2001).
Wilson et al, "Identification and Antigenicity of Broadly Cross-Reactive and Conserved Human Immunodeficiency Virus Type 1-Derived Helper T-Lymphocyte Epitopes", Journal of Virology 75(9):4195-4207 (2001).
Hinkula et al, "Epitope Mapping of the HIV-1 gag Region with Monoclonal Antibodies", Molecular Immunology 27(5):395-403 (1990).
Michel et al, "HIV-1 *Env, Nef*, and *Gag*-specific T-Cell Immunity in Mice: Conserved Epitopes in *Nef*P27 and *Gag* P25 Proteins", AIDS Research and Human Retroviruses 8(4):469-478 (1992).
Mills et al, "HIV p24-specific Helper T Cell Clones from Immunized Primates Recognize Highly Conserved Regions of HIV-1", J. Immunol. 144:1677-1683 (1990).
Nixon et al, "HIV-1 gag-specific Cytotoxic T Lymphocytes Defined with Recombinant Vaccinia Virus and Synthetic Peptides", Nature 336:484-487 (1988).
Baier et al, "HIV Suppression by Interleukin-16", Nature 378:563 (1995).
Goulder et al, "Novel, Cross-Restricted, Conserved, and Immunodominant Cytotoxic T Lymphocyte Epitopes in Slow Progressors in HIV Type I Infection", AIDS Research and Human Retroviruses 12(18):1691-1698 (1996).
Hale et al, "T Cell Multideterminant Regions in the Human Immunodeficiency Virus Envelope: Toward Overcoming the Problem of Major Histocompatibility Complex Restriction", International Immunology 1(4):409-415 (1989).
Loktev et al, "Design of immunogens as components of a new generation of molecular vaccines", Journal of Biotechnology 44(1):129-137 (1996).
U.S. Provisional Application No. 60/503,460 filed Sep. 17, 2003 and U.S. Provisional Application No. 60/604,722 filed Aug. 27, 2004.
U.S. Appl. No. 10/518,523 filed Dec. 21, 2004.
U.S. Appl. No. 10/973,977 filed Oct. 27, 2004.
U.S. Appl. No. 60/625,720 filed Nov. 8, 2004.
Oscherwitz et al, "A V3 loop haptenic peptide sequence, when tandemly repeated, enhances immunogenicity by facilitating helper T-cell responses to a covalently linked carrier protein", Vaccine 17:2392-2399 (1999).
Borbe et al, "Structural and Immunobiological Reactivity of the Principal Neutralizing Determinant V3 of Glycoprotein gp120 of HIV-1", Journal of Peptide Science 1:109-123 (1995).
Winchell et al, "Mucosal Immune Response to an HIV C4/V3 Peptide Following Nasal or Intestinal Immunization of Rabbits", AIDS Research and Human Retroviruses 13(10):881-889 (1997).
Kelleher et al, "Safety and Immunogenicity of UBI HIV-1MN Octameric V3 Peptide Vaccine Administered by Subcutaneous Injection", AIDS Research and Human Retroviruses 13(1):29-32 (1997).
Database Geneseq 'Online!, May 12, 1999, "T cell epitope/ HMC ligand SEQ ID NO:226.", retrieved from EBI accession No. GSN:AAY10296, Database accession No. AAY10296 & WO 99/02183 A (Simard John J L; CTL Immunotherapies Corp (CA); Kuendig Thomas M (CH) Jan. 21, 1999- XP002303500.
Database Geneseq 'Online, Sep. 14, 1999, "HIV-derived lipopeptide epitope GAG253 for mixed micelles", retrieved from EBI accession No. GXN:AAY26615 Database accession No. AAY26615 & WO 99/27954 A (Gras Masse Helene; Guillet Jean Gerard (FR); Inst. Nat. Sante Rech. Med) Jun. 10, 1999-XP002303503.
Database Geneseq 'Online!, Feb. 22, 2000, HLA-A2-binding HIV-1 GP41 CTL Epitope #250, retrieved from EBI accession No. GSN:AAY66448 Database accession No. AAY66448 & WO 99/49893 A (Univ Boston) Oct. 7, 1999—XP002303504.
Gao et al., "Moelcular cloning and analysis of functional envelope genes from human immunodeficiency virus type 1 sequence subtypes A through G. The WHO and NIAID networks for HIV isolation and characterization", Journal of Virology, The American Society for Microbiology 70(3):1651-1667 (1996).
Database Geneseq 'Online!, Nov. 12, 1990, "Peptide component AIDS vaccine.", retrieved from EBI accession No. GSN:AAP2469 Database accession No. AAP82469 & EP 0 273 716 A (US Health) Jul. 6, 1988 XP002303505.

Database USPTO Proteins 'Online!, Oct. 7, 1996, "Sequence 17 from patent US 5519114,", retrieved from EBI accession No. USPOP:AAB13195 Database accession No. AAB13195 & US 5 519 114 A (Johnson Howard M et al) May 21, 1996—XP002303506.

Database EPO Proteins 'Online!, Apr. 26, 1994, "antigen which binds to antibodies with an affinity for HIV-1 p24", retrieved from EBI accession No. EPOP:A18855 Database accession No. A18855 & WO 91/13360 A (Replico Medical AB) Sep. 5, 1991—XP002303507.

Database EPO Proteins 'Online!, Apr. 26, 1994, "antigen which binds to antibodies with an affinity for HIV-1 p24", retrieved from EBI Accession No. EPOP:A18953 Database accession No. A18953 & WO 91/13360 A (Replico Medical AB) Sep. 5, 1991—XP002303508.

Database EPO Proteins 'Online!, Jul. 14, 1993, "Human immunodeficiency virus gag protein", retrieved from EBI accession No. EPOP:A04294 Database accession No. A04294 & WO 86/02383 A (Centre Nat. Rech. Scient. Pasteur Institut (FR) Apr. 24, 1986—XP002303509.

Database EPO Proteins 'Online!, Aug. 23, 1995, "Cytotoxic T lymphocyte epitope 19 derived from gag p17 (MA) protein.", retrieved from EBI accession No. GSN:AAR68762 Database accession No. AAR68762 & WO 94/28871 A (Endocon Inc) Dec. 22, 1994—XP002303510.

Lee et al, "Circulating HIV-1-Infected Cell Burden From Seroconversion to AIDS: Importance of Postseroconversion Viral Load on Disease Course", Journal of Acquired Immune Deficiency Syndromes 7:381-388 (1994).

Rowland-Jones et al, "HIV-specific cytotoxic T-cells in HIV-exposed but uninfected Gambian women", Nature Medicine 1(1):59-64 (1995).

Wain-Hobson et al, "Simon in the Evolutionary biology of viruses, Stephen S. Morse (ed), Raven Press, NY, pp. 185-209 (1994)—Abstract.

Ho et al, "Rapid turnover of plasma virions and CD4 lymphocytes in HIV-1 infection", Nature 373:123-126 (1995).

Robertson et al, "Recombination in AIDS Viruses", Journal of Molecular Evolution 40:249-259 (1995).

Haynes et al, "Use of Synthetic Peptides in Primates to Induce High-Titered Neutralizing Antibodies and MHC Class I-Restricted Cytotoxic T Cells Against Acquired Immunodeficiency Syndrome Retroviruses: An HLA-Based Vaccine Strategy", Transactions of the Association of American Physicians 106:33-41 (1993).

Ward et al, "Analysis of HLA Frequencies in Population Cohorts for Design of HLA-Based HIV Vaccines", HIV Molecular Database, pp. IV-10-IV-16 (1995).

Mayr et al, "The Smallpox Vaccination Strain MVA: Marker, Genetic Structure, Experience Gained with the Parental Vaccination and Behavior in Organisms with a Debilitated Defence Mechanism", Zbl. Bakt. Hyg. I. Abt. Orig. B 167:375-390 (1978).

Bartlett et al, "Safety and immunogenecity of an HLA-based HIV envelope polyvalent synthetic peptide immunogen", AIDS 12:1291-1300 (1998).

Haynes et al, "HIV Type 1 V3 Region Primer-Induced Antibody Suppression Is Overcome by Administration of C4-V3-Peptides as a Polyvalent Immunogen", AIDS Research and Human Retroviruses 11(2):211-221 (1995).

SEQUENCE LISTING

<160> NUMBER OF SEQ ID NOS: 107

<210> SEQ ID NO 1
<211> LENGTH: 10
<212> TYPE: PRT
<213> ORGANISM: Human immunodeficiency virus

<400> SEQUENCE: 1

Gln Val Pro Leu Arg Pro Met Thr Tyr Lys
 1               5                  10

<210> SEQ ID NO 2
<211> LENGTH: 10
<212> TYPE: PRT
<213> ORGANISM: Human immunodeficiency virus

<400> SEQUENCE: 2

Val Glu Arg Tyr Leu Lys Asp Gln Gln Leu
 1               5                  10

<210> SEQ ID NO 3
<211> LENGTH: 12
<212> TYPE: PRT
<213> ORGANISM: Human immunodeficiency virus

<400> SEQUENCE: 3

Arg Arg Ile Arg Gln Gly Leu Glu Arg Ala Leu Leu
 1               5                  10

<210> SEQ ID NO 4
<211> LENGTH: 12
<212> TYPE: PRT
<213> ORGANISM: Human immunodeficiency virus

<400> SEQUENCE: 4

Thr Gln Gly Tyr Phe Pro Asp Trp Gln Asn Tyr Thr
 1               5                  10

<210> SEQ ID NO 5
<211> LENGTH: 9
<212> TYPE: PRT
<213> ORGANISM: Human immunodeficiency virus

<400> SEQUENCE: 5

Ser Phe Asn Cys Gly Gly Glu Phe Phe
 1               5

<210> SEQ ID NO 6
<211> LENGTH: 10
<212> TYPE: PRT
<213> ORGANISM: Human immunodeficiency virus

<400> SEQUENCE: 6

Arg Pro Asn Asn Asn Thr Arg Lys Ser Ile
 1               5                  10

<210> SEQ ID NO 7
<211> LENGTH: 13
<212> TYPE: PRT
<213> ORGANISM: Human immunodeficiency virus

<400> SEQUENCE: 7

Asn Tyr Thr Pro Gly Pro Gly Val Arg Tyr Pro Leu Thr
 1               5                  10

<210> SEQ ID NO 8
<211> LENGTH: 16
<212> TYPE: PRT
<213> ORGANISM: Human immunodeficiency virus

<400> SEQUENCE: 8

```
Ile Pro Met Phe Ser Ala Leu Ser Glu Gly Ala Thr Pro Gln Asp Leu
 1               5                  10                  15
```

<210> SEQ ID NO 9
<211> LENGTH: 7
<212> TYPE: PRT
<213> ORGANISM: Human immunodeficiency virus

<400> SEQUENCE: 9

```
Tyr Leu Lys Asp Gln Gln Leu
 1               5
```

<210> SEQ ID NO 10
<211> LENGTH: 25
<212> TYPE: PRT
<213> ORGANISM: Human immunodeficiency virus

<400> SEQUENCE: 10

```
Tyr Phe Pro Asp Trp Gln Asn Tyr Thr Pro Gly Pro Gly Ile Arg Tyr
 1               5                  10                  15

Pro Leu Thr Phe Gly Trp Cys Tyr Lys
            20                  25
```

<210> SEQ ID NO 11
<211> LENGTH: 11
<212> TYPE: PRT
<213> ORGANISM: Human immunodeficiency virus

<400> SEQUENCE: 11

```
Arg Leu Arg Asp Leu Leu Leu Ile Val Thr Arg
 1               5                  10
```

<210> SEQ ID NO 12
<211> LENGTH: 9
<212> TYPE: PRT
<213> ORGANISM: Human immunodeficiency virus

<400> SEQUENCE: 12

```
Gln Val Leu Arg Pro Met Thr Tyr Lys
 1               5
```

<210> SEQ ID NO 13
<211> LENGTH: 26
<212> TYPE: PRT
<213> ORGANISM: Human immunodeficiency virus

<400> SEQUENCE: 13

```
Tyr Phe Pro Asp Trp Gln Asn Tyr Thr Pro Gly Pro Gly Ile Arg Tyr
 1               5                  10                  15

Pro Leu Thr Phe Cys Gly Trp Cys Tyr Lys
            20                  25
```

<210> SEQ ID NO 14
<211> LENGTH: 31
<212> TYPE: PRT
<213> ORGANISM: Murine sp.

<400> SEQUENCE: 14

```
His Ala Gly Pro Ile Ala Pro Gly Gln Met Arg Glu Pro Arg Gly Lys
 1               5                  10                  15

Gln Ile Ile Asn Met Trp Gln Glu Val Gly Lys Ala Met Tyr Ala
            20                  25                  30
```

```
<210> SEQ ID NO 15
<211> LENGTH: 26
<212> TYPE: PRT
<213> ORGANISM: Murine sp.

<400> SEQUENCE: 15

Lys Glu Lys Val Tyr Leu Ala Trp Val Pro Ala His Lys Gly Ile Gly
 1               5                  10                  15

Met Tyr Ala Pro Pro Ile Gly Gly Gln Ile
            20                  25

<210> SEQ ID NO 16
<211> LENGTH: 30
<212> TYPE: PRT
<213> ORGANISM: Murine sp.

<400> SEQUENCE: 16

Gln Leu Leu Phe Ile His Phe Arg Ile Gly Cys Arg His Ser Arg Asp
 1               5                  10                  15

Arg Val Ile Glu Val Val Gln Gly Ala Tyr Arg Ala Ile Arg
            20                  25                  30

<210> SEQ ID NO 17
<211> LENGTH: 30
<212> TYPE: PRT
<213> ORGANISM: Murine sp.

<400> SEQUENCE: 17

Glu Gln Met His Glu Asp Ile Ile Ser Leu Trp Asp Gln Ser Leu Arg
 1               5                  10                  15

Ile His Ile Gly Pro Gly Arg Ala Phe Tyr Thr Thr Lys Asn
            20                  25                  30

<210> SEQ ID NO 18
<211> LENGTH: 29
<212> TYPE: PRT
<213> ORGANISM: Macaque sp.

<400> SEQUENCE: 18

Glu Leu Tyr Lys Tyr Lys Val Val Lys Ile Glu Pro Leu Gly Val Ala
 1               5                  10                  15

Pro Thr Lys Ala Cys Thr Pro Tyr Asp Ile Asn Gln Met
            20                  25

<210> SEQ ID NO 19
<211> LENGTH: 28
<212> TYPE: PRT
<213> ORGANISM: Macaque sp.

<400> SEQUENCE: 19

Val Ser Thr Val Gln Cys Thr His Gly Ile Arg Pro Val Val Ser Thr
 1               5                  10                  15

Gln Leu Leu Leu Ser Thr Pro Pro Leu Val Arg Leu
            20                  25

<210> SEQ ID NO 20
<211> LENGTH: 29
<212> TYPE: PRT
<213> ORGANISM: Macaque sp.

<400> SEQUENCE: 20

Ser Thr Ser Ile Arg Gly Lys Val Gln Lys Glu Tyr Ala Phe Phe Tyr
```

```
                1               5                  10                 15
Lys Leu Asp Ile Tyr Ala Pro Pro Ile Ser Gly Gln Ile
                     20                  25
```

<210> SEQ ID NO 21
<211> LENGTH: 30
<212> TYPE: PRT
<213> ORGANISM: Macaque sp.

<400> SEQUENCE: 21

```
Val Ser Thr Val Gln Cys Thr His Gly Ile Arg Pro Val Val Ser Thr
1               5                   10                  15
Gln Leu Leu Leu Cys Thr Pro Tyr Asp Tyr Asn Gln Met Leu
                20                  25                  30
```

<210> SEQ ID NO 22
<211> LENGTH: 30
<212> TYPE: PRT
<213> ORGANISM: Macaque sp.

<400> SEQUENCE: 22

```
Ser Thr Ser Ile Arg Gly Lys Val Gln Lys Glu Tyr Ala Phe Phe Tyr
1               5                   10                  15
Lys Leu Asp Ile Cys Thr Pro Tyr Asp Ala Asn Gln Met Leu
                20                  25                  30
```

<210> SEQ ID NO 23
<211> LENGTH: 30
<212> TYPE: PRT
<213> ORGANISM: Macaque sp.

<400> SEQUENCE: 23

```
Glu Tyr Ala Phe Phe Tyr Lys Leu Asp Ile Pro Ile Asp Asn Asp
1               5                   10                  15
Thr Thr Ser Tyr Cys Thr Pro Tyr Asp Asp Asn Gln Met Leu
                20                  25                  30
```

<210> SEQ ID NO 24
<211> LENGTH: 31
<212> TYPE: PRT
<213> ORGANISM: Macaque sp.

<400> SEQUENCE: 24

```
Arg Glu Gln Phe Gly Asn Asn Lys Thr Ile Ile Phe Lys Gln Ser Ser
1               5                   10                  15
Gly Gly Asp Pro Glu Cys Thr Pro Tyr Asp Lys Asn Gln Met Leu
                20                  25                  30
```

<210> SEQ ID NO 25
<211> LENGTH: 27
<212> TYPE: PRT
<213> ORGANISM: Homo sapiens

<400> SEQUENCE: 25

```
Lys Gln Ile Ile Asn Met Trp Gln Glu Val Gly Lys Ala Met Tyr Ala
1               5                   10                  15
Lys Ala Phe Ser Pro Glu Val Ile Pro Met Phe
                20                  25
```

<210> SEQ ID NO 26
<211> LENGTH: 47
<212> TYPE: PRT

```
<213> ORGANISM: Homo sapiens

<400> SEQUENCE: 26

Tyr Lys Arg Trp Ile Ile Leu Gly Leu Asn Lys Ile Val Arg Met Tyr
 1               5                  10                  15

Ser Asn Pro Pro Ile Pro Val Gly Glu Ile Tyr Lys Arg Trp Ile Ile
                20                  25                  30

Leu Gly Leu Asn Lys Ile Val Arg Met Tyr Ser Pro Thr Ser Ile
            35                  40                  45

<210> SEQ ID NO 27
<211> LENGTH: 32
<212> TYPE: PRT
<213> ORGANISM: Homo sapiens

<400> SEQUENCE: 27

Asp Arg Val Ile Glu Val Val Gln Gly Ala Tyr Arg Ala Ile Arg Val
 1               5                  10                  15

Gly Phe Pro Val Arg Pro Gln Val Pro Leu Arg Pro Met Thr Tyr Lys
                20                  25                  30

<210> SEQ ID NO 28
<211> LENGTH: 32
<212> TYPE: PRT
<213> ORGANISM: Homo sapiens

<400> SEQUENCE: 28

Ala Ser Leu Trp Asn Trp Phe Asn Ile Thr Asn Trp Leu Trp Tyr Trp
 1               5                  10                  15

Val Tyr His Thr Gln Gly Phe Phe Pro Asp Trp Gln Asn Tyr Thr Pro
                20                  25                  30

<210> SEQ ID NO 29
<211> LENGTH: 25
<212> TYPE: PRT
<213> ORGANISM: Homo sapiens

<400> SEQUENCE: 29

Lys Gln Ile Ile Asn Met Trp Gln Glu Val Gly Lys Ala Met Tyr Ala
 1               5                  10                  15

Ser Leu Tyr Asn Thr Val Ala Thr Leu
                20                  25

<210> SEQ ID NO 30
<211> LENGTH: 26
<212> TYPE: PRT
<213> ORGANISM: Homo sapiens

<400> SEQUENCE: 30

Tyr Lys Arg Trp Ile Ile Leu Gly Leu Asn Lys Ile Val Arg Met Tyr
 1               5                  10                  15

Ser Lys Ile Arg Leu Arg Pro Gly Gly Lys
                20                  25

<210> SEQ ID NO 31
<211> LENGTH: 25
<212> TYPE: PRT
<213> ORGANISM: Homo sapiens

<400> SEQUENCE: 31

Asp Arg Val Ile Glu Val Val Gln Gly Ala Tyr Arg Ala Ile Arg Lys
 1               5                  10                  15
```

Arg Trp Ile Ile Leu Gly Leu Asn Lys
            20                  25

<210> SEQ ID NO 32
<211> LENGTH: 23
<212> TYPE: PRT
<213> ORGANISM: Homo sapiens

<400> SEQUENCE: 32

Ala Ser Leu Trp Asn Trp Phe Asn Ile Thr Asn Trp Leu Trp Tyr Gly
1               5                   10                  15

Gly Lys Lys Lys Tyr Lys Leu
            20

<210> SEQ ID NO 33
<211> LENGTH: 24
<212> TYPE: PRT
<213> ORGANISM: Homo sapiens

<400> SEQUENCE: 33

Met Arg Glu Pro Arg Gly Ser Lys Ile Ala Gly Thr Thr Ser Thr Glu
1               5                   10                  15

Arg Tyr Leu Lys Asp Gln Gln Leu
            20

<210> SEQ ID NO 34
<211> LENGTH: 26
<212> TYPE: PRT
<213> ORGANISM: Homo sapiens

<400> SEQUENCE: 34

Tyr Lys Arg Trp Ile Ile Leu Gly Leu Asn Lys Ile Val Arg Met Tyr
1               5                   10                  15

Ser Ser Leu Tyr Asn Thr Val Ala Thr Leu
            20                  25

<210> SEQ ID NO 35
<211> LENGTH: 24
<212> TYPE: PRT
<213> ORGANISM: Homo sapiens

<400> SEQUENCE: 35

Asp Arg Val Ile Glu Val Val Gln Gly Ala Tyr Arg Ala Ile Arg Ser
1               5                   10                  15

Leu Phe Asn Thr Val Ala Thr Leu
            20

<210> SEQ ID NO 36
<211> LENGTH: 24
<212> TYPE: PRT
<213> ORGANISM: Homo sapiens

<400> SEQUENCE: 36

Gln Ile Ile Asn Met Trp Gln Glu Val Gly Lys Ala Met Tyr Ala Ser
1               5                   10                  15

Leu Tyr Asn Ala Val Ala Thr Leu
            20

<210> SEQ ID NO 37
<211> LENGTH: 24
<212> TYPE: PRT
<213> ORGANISM: Homo sapiens

<400> SEQUENCE: 37

Ala Ser Leu Trp Asn Trp Phe Asn Ile Thr Asn Trp Leu Trp Tyr Ser
1               5                   10                  15

Leu Tyr Asn Thr Val Ala Val Leu
            20

<210> SEQ ID NO 38
<211> LENGTH: 24
<212> TYPE: PRT
<213> ORGANISM: Homo sapiens

<400> SEQUENCE: 38

Met Arg Glu Pro Arg Gly Ser Lys Ile Ala Gly Thr Thr Ser Thr Ser
1               5                   10                  15

Leu Phe Asn Leu Leu Ala Val Leu
            20

<210> SEQ ID NO 39
<211> LENGTH: 36
<212> TYPE: PRT
<213> ORGANISM: Homo sapiens

<400> SEQUENCE: 39

Lys Gln Ile Ile Asn Met Trp Gln Val Val Gly Lys Ala Met Tyr Ala
1               5                   10                  15

Gly Gln Met Val His Gln Ala Ile Ser Pro Arg Thr Leu Asn Ala Trp
            20                  25                  30

Val Lys Val Val
        35

<210> SEQ ID NO 40
<211> LENGTH: 50
<212> TYPE: PRT
<213> ORGANISM: Homo sapiens

<400> SEQUENCE: 40

Lys Gln Ile Ile Asn Met Trp Gln Val Val Gly Lys Ala Met Tyr Ala
1               5                   10                  15

Ala Thr Pro Gln Asp Leu Asn Thr Met Leu Asn Thr Val Gly Gly His
            20                  25                  30

Gln Ala Ala Met Gln Met Leu Lys Glu Thr Ile Asn Glu Glu Ala Ala
        35                  40                  45

Glu Trp
    50

<210> SEQ ID NO 41
<211> LENGTH: 47
<212> TYPE: PRT
<213> ORGANISM: Homo sapiens

<400> SEQUENCE: 41

Lys Gln Ile Ile Asn Met Trp Gln Val Val Gly Lys Ala Met Tyr Ala
1               5                   10                  15

Gly Pro Lys Glu Pro Phe Arg Asp Tyr Val Asp Arg Phe Tyr Lys Thr
            20                  25                  30

Leu Arg Ala Glu Gln Ala Ser Gln Glu Val Lys Asn Trp Met Thr
        35                  40                  45

<210> SEQ ID NO 42

```
<211> LENGTH: 57
<212> TYPE: PRT
<213> ORGANISM: Homo sapiens

<400> SEQUENCE: 42

Lys Gln Ile Ile Asn Met Trp Gln Val Val Gly Lys Ala Met Tyr Ala
 1               5                  10                  15

Lys Ile Arg Leu Arg Pro Gly Gly Lys Lys Lys Tyr Lys Leu Lys His
            20                  25                  30

Ile Val Trp Gly Ser Glu Glu Leu Arg Ser Leu Tyr Asn Thr Val Ala
        35                  40                  45

Thr Leu Tyr Cys Val His Gln Arg Ile
    50                  55

<210> SEQ ID NO 43
<211> LENGTH: 15
<212> TYPE: PRT
<213> ORGANISM: Murine sp.

<400> SEQUENCE: 43

His Ala Gly Pro Ile Ala Pro Gly Gln Met Arg Glu Pro Arg Gly
 1               5                  10                  15

<210> SEQ ID NO 44
<211> LENGTH: 16
<212> TYPE: PRT
<213> ORGANISM: Murine sp.

<400> SEQUENCE: 44

Lys Gln Ile Ile Asn Met Trp Gln Glu Val Gly Lys Ala Met Tyr Ala
 1               5                  10                  15

<210> SEQ ID NO 45
<211> LENGTH: 16
<212> TYPE: PRT
<213> ORGANISM: Murine sp.

<400> SEQUENCE: 45

Lys Glu Lys Val Tyr Leu Ala Trp Val Pro Ala His Lys Gly Ile Gly
 1               5                  10                  15

<210> SEQ ID NO 46
<211> LENGTH: 10
<212> TYPE: PRT
<213> ORGANISM: Murine sp.

<400> SEQUENCE: 46

Met Tyr Ala Pro Pro Ile Gly Gly Gln Ile
 1               5                  10

<210> SEQ ID NO 47
<211> LENGTH: 15
<212> TYPE: PRT
<213> ORGANISM: Murine sp.

<400> SEQUENCE: 47

Gln Leu Leu Phe Ile His Phe Arg Ile Gly Cys Arg His Ser Arg
 1               5                  10                  15

<210> SEQ ID NO 48
<211> LENGTH: 15
<212> TYPE: PRT
<213> ORGANISM: Murine sp.
```

-continued

<400> SEQUENCE: 48

Asp Arg Val Ile Glu Val Val Gln Gly Ala Tyr Arg Ala Ile Arg
 1               5                  10                  15

<210> SEQ ID NO 49
<211> LENGTH: 15
<212> TYPE: PRT
<213> ORGANISM: Murine sp.

<400> SEQUENCE: 49

Glu Gln Met His Glu Asp Ile Ile Ser Leu Trp Asp Gln Ser Leu
 1               5                  10                  15

<210> SEQ ID NO 50
<211> LENGTH: 15
<212> TYPE: PRT
<213> ORGANISM: Murine sp.

<400> SEQUENCE: 50

Arg Ile His Ile Gly Pro Gly Arg Ala Phe Tyr Thr Thr Lys Asn
 1               5                  10                  15

<210> SEQ ID NO 51
<211> LENGTH: 20
<212> TYPE: PRT
<213> ORGANISM: Macaque sp.

<400> SEQUENCE: 51

Glu Leu Tyr Lys Tyr Lys Val Val Lys Ile Glu Pro Leu Gly Val Ala
 1               5                  10                  15

Pro Thr Lys Ala
            20

<210> SEQ ID NO 52
<211> LENGTH: 9
<212> TYPE: PRT
<213> ORGANISM: Macaque sp.

<400> SEQUENCE: 52

Cys Thr Pro Tyr Asp Ile Asn Gln Met
 1               5

<210> SEQ ID NO 53
<211> LENGTH: 20
<212> TYPE: PRT
<213> ORGANISM: Macaque sp.

<400> SEQUENCE: 53

Val Ser Thr Val Gln Cys Thr His Gly Ile Arg Pro Val Val Ser Thr
 1               5                  10                  15

Gln Leu Leu Leu
            20

<210> SEQ ID NO 54
<211> LENGTH: 8
<212> TYPE: PRT
<213> ORGANISM: Macaque sp.

<400> SEQUENCE: 54

Ser Thr Pro Pro Leu Val Arg Leu
 1               5

<210> SEQ ID NO 55

```
<211> LENGTH: 20
<212> TYPE: PRT
<213> ORGANISM: Macaque sp.

<400> SEQUENCE: 55

Ser Thr Ser Ile Arg Gly Lys Val Gln Lys Glu Tyr Ala Phe Phe Tyr
 1               5                  10                  15

Lys Leu Asp Ile
            20

<210> SEQ ID NO 56
<211> LENGTH: 9
<212> TYPE: PRT
<213> ORGANISM: Macaque sp.

<400> SEQUENCE: 56

Tyr Ala Pro Pro Ile Ser Gly Gln Ile
 1               5

<210> SEQ ID NO 57
<211> LENGTH: 20
<212> TYPE: PRT
<213> ORGANISM: Macaque sp.

<400> SEQUENCE: 57

Glu Leu Tyr Lys Tyr Lys Val Val Lys Ile Glu Pro Leu Gly Val Ala
 1               5                  10                  15

Pro Thr Lys Ala
            20

<210> SEQ ID NO 58
<211> LENGTH: 10
<212> TYPE: PRT
<213> ORGANISM: Macaque sp.

<400> SEQUENCE: 58

Cys Thr Pro Tyr Asp Ile Asn Gln Met Leu
 1               5                  10

<210> SEQ ID NO 59
<211> LENGTH: 20
<212> TYPE: PRT
<213> ORGANISM: Macaque sp.

<400> SEQUENCE: 59

Val Ser Thr Val Gln Cys Thr His Gly Ile Arg Pro Val Val Ser Thr
 1               5                  10                  15

Gln Leu Leu Leu
            20

<210> SEQ ID NO 60
<211> LENGTH: 10
<212> TYPE: PRT
<213> ORGANISM: Macaque sp.

<400> SEQUENCE: 60

Cys Thr Pro Tyr Asp Tyr Asn Gln Met Leu
 1               5                  10

<210> SEQ ID NO 61
<211> LENGTH: 20
<212> TYPE: PRT
<213> ORGANISM: Macaque sp.

<400> SEQUENCE: 61
```

Ser Thr Ser Ile Arg Gly Lys Val Gln Lys Glu Tyr Ala Phe Phe Tyr
 1               5                  10                  15

Lys Leu Asp Ile
            20

<210> SEQ ID NO 62
<211> LENGTH: 10
<212> TYPE: PRT
<213> ORGANISM: Macaque sp.

<400> SEQUENCE: 62

Cys Thr Pro Tyr Asp Ala Asn Gln Met Leu
 1               5                  10

<210> SEQ ID NO 63
<211> LENGTH: 20
<212> TYPE: PRT
<213> ORGANISM: Macaque sp.

<400> SEQUENCE: 63

Glu Tyr Ala Phe Phe Tyr Lys Leu Asp Ile Ile Pro Ile Asp Asn Asp
 1               5                  10                  15

Thr Thr Ser Tyr
            20

<210> SEQ ID NO 64
<211> LENGTH: 10
<212> TYPE: PRT
<213> ORGANISM: Macaque sp.

<400> SEQUENCE: 64

Cys Thr Pro Tyr Asp Asp Asn Gln Met Leu
 1               5                  10

<210> SEQ ID NO 65
<211> LENGTH: 21
<212> TYPE: PRT
<213> ORGANISM: Macaque sp.

<400> SEQUENCE: 65

Arg Glu Gln Phe Gly Asn Asn Lys Thr Ile Ile Phe Lys Gln Ser Ser
 1               5                  10                  15

Gly Gly Asp Pro Glu
            20

<210> SEQ ID NO 66
<211> LENGTH: 10
<212> TYPE: PRT
<213> ORGANISM: Macaque sp.

<400> SEQUENCE: 66

Cys Thr Pro Tyr Asp Lys Asn Gln Met Leu
 1               5                  10

<210> SEQ ID NO 67
<211> LENGTH: 16
<212> TYPE: PRT
<213> ORGANISM: Homo sapiens

<400> SEQUENCE: 67

Lys Gln Ile Ile Asn Met Trp Gln Glu Val Gly Lys Ala Met Tyr Ala
 1               5                  10                  15

```
<210> SEQ ID NO 68
<211> LENGTH: 11
<212> TYPE: PRT
<213> ORGANISM: Homo sapiens

<400> SEQUENCE: 68

Lys Ala Phe Ser Pro Glu Val Ile Pro Met Phe
 1               5                  10

<210> SEQ ID NO 69
<211> LENGTH: 17
<212> TYPE: PRT
<213> ORGANISM: Homo sapiens

<400> SEQUENCE: 69

Tyr Lys Arg Trp Ile Ile Leu Gly Leu Asn Lys Ile Val Arg Met Tyr
 1               5                  10                  15

Ser

<210> SEQ ID NO 70
<211> LENGTH: 30
<212> TYPE: PRT
<213> ORGANISM: Homo sapiens

<400> SEQUENCE: 70

Asn Pro Pro Ile Pro Val Gly Glu Ile Tyr Lys Arg Trp Ile Ile Leu
 1               5                  10                  15

Gly Leu Asn Lys Ile Val Arg Met Tyr Ser Pro Thr Ser Ile
            20                  25                  30

<210> SEQ ID NO 71
<211> LENGTH: 15
<212> TYPE: PRT
<213> ORGANISM: Homo sapiens

<400> SEQUENCE: 71

Asp Arg Val Ile Glu Val Val Gln Gly Ala Tyr Arg Ala Ile Arg
 1               5                  10                  15

<210> SEQ ID NO 72
<211> LENGTH: 17
<212> TYPE: PRT
<213> ORGANISM: Homo sapiens

<400> SEQUENCE: 72

Val Gly Phe Pro Val Arg Pro Gln Val Pro Leu Arg Pro Met Thr Tyr
 1               5                  10                  15

Lys

<210> SEQ ID NO 73
<211> LENGTH: 15
<212> TYPE: PRT
<213> ORGANISM: Homo sapiens

<400> SEQUENCE: 73

Ala Ser Leu Trp Asn Trp Phe Asn Ile Thr Asn Trp Leu Trp Tyr
 1               5                  10                  15

<210> SEQ ID NO 74
<211> LENGTH: 17
<212> TYPE: PRT
<213> ORGANISM: Homo sapiens
```

```
<400> SEQUENCE: 74

Trp Val Tyr His Thr Gln Gly Phe Phe Pro Asp Trp Gln Asn Tyr Thr
  1               5                  10                  15
Pro

<210> SEQ ID NO 75
<211> LENGTH: 16
<212> TYPE: PRT
<213> ORGANISM: Artificial Sequence
<220> FEATURE:
<223> OTHER INFORMATION: Description of Artificial Sequence: HIV-1
      Th-dominant/subdominant CTL epitopes in MVA.

<400> SEQUENCE: 75

Lys Gln Ile Ile Asn Met Trp Gln Glu Val Gly Lys Ala Met Tyr Ala
  1               5                  10                  15

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: HIV-1
      Th-dominant/subdominant CTL epitopes in MVA.

<400> SEQUENCE: 76

Ser Leu Tyr Asn Thr Val Ala Thr Leu
  1               5

<210> SEQ ID NO 77
<211> LENGTH: 17
<212> TYPE: PRT
<213> ORGANISM: Artificial Sequence
<220> FEATURE:
<223> OTHER INFORMATION: Description of Artificial Sequence: HIV-1
      Th-dominant/subdominant CTL epitopes in MVA.

<400> SEQUENCE: 77

Tyr Lys Arg Trp Ile Ile Leu Gly Leu Asn Lys Ile Val Arg Met Tyr
  1               5                  10                  15
Ser

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: HIV-1
      Th-dominant/subdominant CTL epitopes in MVA.

<400> SEQUENCE: 78

Lys Ile Arg Leu Arg Pro Gly Gly Lys
  1               5

<210> SEQ ID NO 79
<211> LENGTH: 15
<212> TYPE: PRT
<213> ORGANISM: Artificial Sequence
<220> FEATURE:
<223> OTHER INFORMATION: Description of Artificial Sequence: HIV-1
      Th-dominant/subdominant CTL epitopes in MVA.

<400> SEQUENCE: 79

Asp Arg Val Ile Glu Val Val Gln Gly Ala Tyr Arg Ala Ile Arg
  1               5                  10                  15
```

```
<210> SEQ ID NO 80
<211> LENGTH: 10
<212> TYPE: PRT
<213> ORGANISM: Artificial Sequence
<220> FEATURE:
<223> OTHER INFORMATION: Description of Artificial Sequence: HIV-1
      Th-dominant/subdominant CTL epitopes in MVA.

<400> SEQUENCE: 80

Lys Arg Trp Ile Ile Leu Gly Leu Asn Lys
 1               5                  10

<210> SEQ ID NO 81
<211> LENGTH: 15
<212> TYPE: PRT
<213> ORGANISM: Artificial Sequence
<220> FEATURE:
<223> OTHER INFORMATION: Description of Artificial Sequence: HIV-1
      Th-dominant/subdominant CTL epitopes in MVA.

<400> SEQUENCE: 81

Ala Ser Leu Trp Asn Trp Phe Asn Ile Thr Asn Trp Leu Trp Tyr
 1               5                  10                  15

<210> SEQ ID NO 82
<211> LENGTH: 8
<212> TYPE: PRT
<213> ORGANISM: Artificial Sequence
<220> FEATURE:
<223> OTHER INFORMATION: Description of Artificial Sequence: HIV-1
      Th-dominant/subdominant CTL epitopes in MVA.

<400> SEQUENCE: 82

Gly Gly Lys Lys Lys Tyr Lys Leu
 1               5

<210> SEQ ID NO 83
<211> LENGTH: 15
<212> TYPE: PRT
<213> ORGANISM: Artificial Sequence
<220> FEATURE:
<223> OTHER INFORMATION: Description of Artificial Sequence: HIV-1
      Th-dominant/subdominant CTL epitopes in MVA.

<400> SEQUENCE: 83

Met Arg Glu Pro Arg Gly Ser Lys Ile Ala Gly Thr Thr Ser Thr
 1               5                  10                  15

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: HIV-1
      Th-dominant/subdominant CTL epitopes in MVA.

<400> SEQUENCE: 84

Glu Arg Tyr Leu Lys Asp Gln Gln Leu
 1               5

<210> SEQ ID NO 85
<211> LENGTH: 17
<212> TYPE: PRT
<213> ORGANISM: Artificial Sequence
<220> FEATURE:
<223> OTHER INFORMATION: Description of Artificial Sequence: HIV-1 Th
      -CTL A2 p17 epitope (A2 Variants) in MVA
```

```
-continued

<400> SEQUENCE: 85

Tyr Lys Arg Trp Ile Ile Leu Gly Leu Asn Lys Ile Val Arg Met Tyr
 1               5                  10                  15

Ser

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: HIV-1 Th
      -CTL A2 p17 epitope (A2 Variants) in MVA

<400> SEQUENCE: 86

Ser Leu Tyr Asn Thr Val Ala Thr Leu
 1               5

<210> SEQ ID NO 87
<211> LENGTH: 15
<212> TYPE: PRT
<213> ORGANISM: Artificial Sequence
<220> FEATURE:
<223> OTHER INFORMATION: Description of Artificial Sequence: HIV-1 Th
      -CTL A2 p17 epitope (A2 Variants) in MVA

<400> SEQUENCE: 87

Asp Arg Val Ile Glu Val Val Gln Gly Ala Tyr Arg Ala Ile Arg
 1               5                  10                  15

<210> SEQ ID NO 88
<211> LENGTH: 9
<212> TYPE: PRT
<213> ORGANISM: Artificial Sequence
<220> FEATURE:
<223> OTHER INFORMATION: Description of Artificial Sequence: HIV-1 Th
      -CTL A2 p17 epitope (A2 Variants) in MVA

<400> SEQUENCE: 88

Ser Leu Phe Asn Thr Val Ala Thr Leu
 1               5

<210> SEQ ID NO 89
<211> LENGTH: 16
<212> TYPE: PRT
<213> ORGANISM: Artificial Sequence
<220> FEATURE:
<223> OTHER INFORMATION: Description of Artificial Sequence: HIV-1
      Th-CTL A2 p17 epitope (A2 Variants) in MVA

<400> SEQUENCE: 89

Lys Gln Ile Ile Asn Met Trp Gln Glu Val Gly Lys Ala Met Tyr Ala
 1               5                  10                  15

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: HIV-1
      Th-CTL A2 p17 epitope (A2 Variants) in MVA

<400> SEQUENCE: 90

Ser Leu Tyr Asn Ala Val Ala Thr Leu
 1               5

<210> SEQ ID NO 91
```

```
<211> LENGTH: 15
<212> TYPE: PRT
<213> ORGANISM: Artificial Sequence
<220> FEATURE:
<223> OTHER INFORMATION: Description of Artificial Sequence: HIV-1
      Th-CTL A2 p17 epitope (A2 Variants) in MVA

<400> SEQUENCE: 91

Ala Ser Leu Trp Asn Trp Phe Asn Ile Thr Asn Trp Leu Trp Tyr
1               5                   10                  15

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: HIV-1
      Th-CTL A2 p17 epitope (A2 Variants) in MVA

<400> SEQUENCE: 92

Ser Leu Tyr Asn Thr Val Ala Val Leu
1               5

<210> SEQ ID NO 93
<211> LENGTH: 15
<212> TYPE: PRT
<213> ORGANISM: Artificial Sequence
<220> FEATURE:
<223> OTHER INFORMATION: Description of Artificial Sequence: HIV-1
      Th-CTL A2 p17 epitope (A2 Variants) in MVA

<400> SEQUENCE: 93

Met Arg Glu Pro Arg Gly Ser Lys Ile Ala Gly Thr Thr Ser Thr
1               5                   10                  15

<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: HIV-1
      Th-CTL A2 p17 epitope (A2 Variants) in MVA

<400> SEQUENCE: 94

Ser Leu Phe Asn Leu Leu Ala Val Leu
1               5

<210> SEQ ID NO 95
<211> LENGTH: 39
<212> TYPE: PRT
<213> ORGANISM: Human immunodeficiency virus

<400> SEQUENCE: 95

Lys Gln Ile Ile Asn Met Trp Gln Glu Val Gly Lys Ala Met Tyr Ala
1               5                   10                  15

Thr Arg Pro Asn Tyr Asn Lys Arg Lys Arg Ile His Ile Gly Pro Gly
            20                  25                  30

Arg Ala Phe Tyr Thr Thr Lys
        35

<210> SEQ ID NO 96
<211> LENGTH: 39
<212> TYPE: PRT
<213> ORGANISM: Human immunodeficiency virus

<400> SEQUENCE: 96
```

```
Lys Gln Ile Ile Asn Met Trp Gln Glu Val Gly Lys Ala Met Tyr Ala
 1               5                  10                  15

Thr Arg Pro Asn Asn Thr Arg Lys Ser Ile Thr Lys Gly Pro Gly
            20                  25                  30

Arg Val Ile Tyr Ala Thr Gly
            35

<210> SEQ ID NO 97
<211> LENGTH: 39
<212> TYPE: PRT
<213> ORGANISM: Human immunodeficiency virus

<400> SEQUENCE: 97

Lys Gln Ile Ile Asn Met Trp Gln Glu Val Gly Lys Ala Met Tyr Ala
 1               5                  10                  15

Thr Arg Pro Gly Asn Asn Thr Arg Lys Ser Ile Pro Ile Gly Pro Gly
            20                  25                  30

Arg Ala Phe Ile Ala Thr Ser
            35

<210> SEQ ID NO 98
<211> LENGTH: 39
<212> TYPE: PRT
<213> ORGANISM: Human immunodeficiency virus

<400> SEQUENCE: 98

Lys Gln Ile Ile Asn Met Trp Gln Glu Val Gly Lys Ala Met Tyr Ala
 1               5                  10                  15

Thr Arg Pro His Asn Asn Thr Arg Lys Ser Ile His Met Gly Pro Gly
            20                  25                  30

Lys Ala Phe Tyr Thr Thr Gly
            35

<210> SEQ ID NO 99
<211> LENGTH: 39
<212> TYPE: PRT
<213> ORGANISM: Human immunodeficiency virus

<400> SEQUENCE: 99

Lys Gln Ile Ile Asn Met Trp Gln Gly Val Gly Lys Ala Met Tyr Ala
 1               5                  10                  15

Thr Arg Pro Asn Asn Thr Arg Lys Ser Ile Thr Lys Gly Pro Gly
            20                  25                  30

Arg Val Ile Tyr Ala Thr Gly
            35

<210> SEQ ID NO 100
<211> LENGTH: 39
<212> TYPE: PRT
<213> ORGANISM: Human immunodeficiency virus

<400> SEQUENCE: 100

Lys Gln Ile Ile Asn Met Trp Gln Val Val Gly Lys Ala Met Tyr Ala
 1               5                  10                  15

Thr Arg Pro Asn Asn Thr Arg Lys Ser Ile Thr Lys Gly Pro Gly
            20                  25                  30

Arg Val Ile Tyr Ala Thr Gly
            35

<210> SEQ ID NO 101
```

-continued

<211> LENGTH: 39
<212> TYPE: PRT
<213> ORGANISM: Human immunodeficiency virus

<400> SEQUENCE: 101

Lys Gln Ile Ile Asn Met Trp Gln Glu Val Gly Glu Ala Met Tyr Ala
 1               5                  10                  15

Thr Arg Pro Asn Asn Asn Thr Arg Lys Ser Ile Thr Lys Gly Pro Gly
            20                  25                  30

Arg Val Ile Tyr Ala Thr Gly
        35

<210> SEQ ID NO 102
<211> LENGTH: 27
<212> TYPE: PRT
<213> ORGANISM: Homo sapiens

<400> SEQUENCE: 102

Lys Gln Ile Ile Asn Met Trp Gln Glu Val Gly Lys Ala Met Tyr Ala
 1               5                  10                  15

Lys Ala Phe Ser Pro Glu Val Ile Pro Met Phe
            20                  25

SEQ ID NO 103
<211> LENGTH: 47
<212> TYPE: PRT
<213> ORGANISM: Homo sapiens

<400> SEQUENCE: 103

Tyr Lys Arg Trp Ile Ile Leu Gly Leu Asn Lys Ile Val Arg Met Tyr
 1               5                  10                  15

Ser Asn Pro Pro Ile Pro Val Gly Glu Ile Tyr Lys Arg Trp Ile Ile
            20                  25                  30

Leu Gly Leu Asn Lys Ile Val Arg Met Tyr Ser Pro Thr Ser Ile
        35                  40                  45

<210> SEQ ID NO 104
<211> LENGTH: 36
<212> TYPE: PRT
<213> ORGANISM: Homo sapiens

<400> SEQUENCE: 104

Lys Gln Ile Ile Asn Met Trp Gln Val Val Gly Lys Ala Met Tyr Ala
 1               5                  10                  15

Gly Gln Met Val His Gln Ala Ile Ser Pro Arg Thr Leu Asn Ala Trp
            20                  25                  30

Val Lys Val Val
        35

<210> SEQ ID NO 105
<211> LENGTH: 50
<212> TYPE: PRT
<213> ORGANISM: Homo sapiens

<400> SEQUENCE: 105

Lys Gln Ile Ile Asn Met Trp Gln Val Val Gly Lys Ala Met Tyr Ala
 1               5                  10                  15

Ala Thr Pro Gln Asp Leu Asn Thr Met Leu Asn Thr Val Gly Gly His
            20                  25                  30

Gln Ala Ala Met Gln Met Leu Lys Glu Thr Ile Asn Glu Glu Ala Ala

```
                    35                  40                  45
Glu Trp
         50

<210> SEQ ID NO 106
<211> LENGTH: 47
<212> TYPE: PRT
<213> ORGANISM: Homo sapiens

<400> SEQUENCE: 106

Lys Gln Ile Ile Asn Met Trp Gln Val Val Gly Lys Ala Met Tyr Ala
  1               5                  10                  15

Gly Pro Lys Glu Pro Phe Arg Asp Tyr Val Asp Arg Phe Tyr Lys Thr
             20                  25                  30

Leu Arg Ala Glu Gln Ala Ser Gln Glu Val Lys Asn Trp Met Thr
         35                  40                  45

<210> SEQ ID NO 107
<211> LENGTH: 57
<212> TYPE: PRT
<213> ORGANISM: Homo sapiens

<400> SEQUENCE: 107

Lys Gln Ile Ile Asn Met Trp Gln Val Val Gly Lys Ala Met Tyr Ala
  1               5                  10                  15

Lys Ile Arg Leu Arg Pro Gly Gly Lys Lys Tyr Lys Leu Lys His
             20                  25                  30

Ile Val Trp Gly Ser Glu Glu Leu Arg Ser Leu Tyr Asn Thr Val Ala
         35                  40                  45

Thr Leu Tyr Cys Val His Gln Arg Ile
         50                  55
```

IMMUNOGENIC COMPOSITION

This application is a division of application Ser. No. 09/775,805, filed Feb. 5, 2001 now U.S. Pat. No. 6,982,086 which is a continuation-in-part of application Ser. No. 09/497,497, filed Feb. 4, 2000, now abandoned, the entire contents of which are hereby incorporated herein by reference.

TECHNICAL FIELD

The present invention relates, in general, to human immunodeficiency virus (HIV) and, in particular, to an HLA-based HIV vaccine.

BACKGROUND

As the HIV epidemic continues to spread world-wide, the need for an effective HIV vaccine remains urgent. The extraordinary ability of HIV to mutate, the inability of many currently known specificities of anti-HIV antibodies to consistently neutralize HIV primary isolates, and the lack of a complete understanding of the correlates of protective immunity to HIV infection have impeded efforts to develop an HIV vaccine having the desired effectiveness.

Although a majority of HIV-infected subjects develop acquired immunodeficiency syndrome (AIDS), approximately 10–15% of patients are AIDS-free after 10 years of infection, and are termed non-progressors to AIDS (Sheppard et al, AIDS 7:1159–66 (1993), Phair, AIDS Res. Human Retroviruses 10:883–885 (1994)). Of those that do develop AIDS, those that do develop AIDS, approximately 10% of HIV-infected patients progress to AIDS within the first two to three years of HIV infection, and are termed rapid progressors to AIDS (Sheppard et al, AIDS 7:1159–66 (1993), Phair, AIDS Res. Human Retroviruses 10:883–885 (1994)). The initial characterization of anti-HIV immune responses in non-progressors and rapid progressors to AIDS has provided some insight into what may be the correlates of protective immunity to HIV.

In general, rapid progressors to AIDS have lower levels of antibodies to HIV proteins (Sheppard et al, AIDS 7:1159–66 (1993), Pantaleo et al, N. Engl. J. Med. 332:209–216 (1995), Cao et al, N. Eng. J. Med. 332:201–208 (1995)), and low or absent antibodies that neutralize autologous HIV isolates (Pantaleo et al, N. Engl. J. Med. 332:209–216 (1995), Cao et al, N. Eng. J. Med. 332:201–208 (1995)). Anti-HIV CD8+ CTL activity is present in peripheral blood T cells of rapid progressors, although one study has found low levels of memory CD8+ CTL by precursor frequency analysis in rapid progressors versus non-progressors (Pantaleo et al, Nature 370:463–467 (1994), Rinaldo, personal communication (1995)). Plasma levels of HIV virions are generally higher in rapid progressors compared to non-progressors, and rapidly replicating HIV strains are isolated more frequently from rapid progressors (Lee et al, J. AIDS 7:381–388 (1994), Mellors et al, Ann. Intern. Med. 122:573–579 (1995), Jurriaans et al, Virology 204:223–233 (1994)), either as a consequence of immunodeficiency and selection of more virulent HIV variants, or as a consequence of more virulent HIV variants infecting rapid progressors (Sullivan et al, J. Virol. 69:4413–4422 (1995)). Taken together with data that the fall in plasma viremia in primary HIV infection correlates with the presence of CD8+ anti-HIV CTL activity (Borrow et al, J. Virol. 68:6103 (1994)), these data suggest that anti-HIV CD8+ CTL that kill HIV-infected cells and antibodies that broadly neutralize HIV primary isolates, might be protective anti-HIV immune responses in uninfected individuals subsequently exposed to HIV (Haynes et al, Science 271:324–328 (1996), Haynes, Science 260:1279–1286 (1993)).

It has been suggested that less effective anti-HIV CD8+ CTL responses may be oligoclonal regarding TCR Vβ usage and targeted at several non-immunodominant HIV CTL epitopes, whereas more effective anti-HIV CTL responses may be polyclonal and targeted at fewer immunodominant epitopes (Rowland-Jones et al, Nature Medicine 1:59–64 (1995), Nowak et al, Nature 375:606–611 (1995)). Taken together with data that suggest the inheritance of certain HLA-encoded or other host genes may be associated with either rapid progression or non-progression to AIDS (Haynes et al, Science 271:324–328 (1996)), these data suggest that host gene expression may determine the quality and/or quantity of host anti-HIV immune responses.

Potent non-HLA restricted CD8+ T cell anti-HIV activity that suppresses the ability of HIV to replicate has been described by Levy et al (Walker et al, Science 234:1563–1566 (1986)). This CD8+ "HIV suppressor" activity is initially present in rapid progressors, then declines with the onset of AIDS (Walker et al, Science 234:1563–1566 (1986)), and may be mediated in part by cytokines such as IL-16 (Baier et al, Nature 378:563 (1995)), and by the chemokines, RANTES, MIP-1a and MIP-1b (Cocchi et al, Science 270:1811–1815 (1995)). Berger and colleagues have recently discovered a novel host molecule termed fusin, that is required for T cell tropic HIV to infect CD4+ T cells, and has significant homology with a known chemokine receptor, the IL8 receptor (Feng et al, Science 272:872–877 (1996)).

Thus, for induction of CD8+ "HIV suppressor" cells, CD8+ CTL and CD4+ T helper cells by an HIV immunogen, what is most likely needed are immunogens that induce these anti-HIV responses to a sufficient number of HIV variants such that a majority of HIV variants in a geographic area will be recognized.

A key obstacle to HIV vaccine development is the extraordinary variability of HIV and the rapidity and extent of HIV mutation (Win-Hobson in The Evolutionary biology of Retroviruses, SSB Morse Ed. Raven Press, N.Y., pgs 185–209 (1994)). Recent data in patients treated with anti-retroviral drugs have demonstrated that HIV variants emerge rapidly after initiation of treatment and can be isolated from peripheral blood as early as 3 weeks after initiation of drug treatment (Wei et al, Nature 373:117–122 (1995), Ho et al, Nature 373:123 (1995)). Moreover, up to $10^9$ new HIV virions are produced in an infected individual per day, and the half-life of HIV quasispecies is approximately 2 days (Wei et al, Nature 373:117–122 (1995), Ho et al, Nature 373:123 (1995)).

Myers, Korber and colleagues have analyzed HIV sequences worldwide and divided HIV isolates into groups or clades, and provided a basis for evaluating the evolutionary relationship of individual HIV isolates to each other (Myers et al (Eds), Human Retroviruses and AIDS (1995), Published by Theoretical Biology and Biophysics Group, T-10, Mail Stop K710, Los Alamos National Laboratory, Los Alamos, N. Mex. 87545). The degree of variation in HIV protein regions that contain CTL and T helper epitopes has also recently been analyzed by Korber et al, and sequence variation documented in many CTL and T helper epitopes among HIV isolates (Korber et al (Eds), HIV Molecular Immunology Database (1995), Published by Theoretical Biology and Biophysics Group, Los Alamos National Laboratory, Los Alamos, N. Mex. 87545).

A new level of HIV variation complexity was recently reported by Hahn et al. by demonstrating the frequent recombination of HIV among clades (Robinson et al, J. Mol. Evol. 40:245–259 (1995)). These authors suggest that as many as 10% of HIV isolates are mosaics of recombination, suggesting that vaccines based on only one HIV clade will not protect immunized subjects from mosaic HIV isolates (Robinson et al, J. Mol. Evol. 40:245–259 (1995)).

The large number of HIV variants available for transmission and the possible immunodominant nature of what may be protective anti-HIV T cell responses has suggested the need for consideration of development of HLA-based HIV subunit vaccines (Palker et al, J. Immunol. 142:3612–3619 (1989), Berzofsky, FASEB Journal 5:2412 (1991), Haynes et al, Trans. Assoc. Amer. Phys. 106:33–41 (1993), Haynes et al, AIDS Res. Human. Retroviral. 11:211 (1995), Ward et al, In Lost Alamos Database (1995), B. Korber (Ed). In press, Cease et al, Ann. Rev. Immunol. 12:923–989 (1994)). The present invention provides such a vaccine.

SUMMARY OF THE INVENTION

The present invention relates to an HLA-based vaccine against HIV. Vaccines of the invention, which induce salutary anti-HIV immune responses, can be designed based on analysis of the HLA alleles present in the cohort to be immunized and analysis of the most common HIV variants present in the geographic location of the cohort. The invention also relates to a method of immunizing a patient against HIV using the HLA-based vaccine.

Objects and advantages of the present invention will be clear from the description that follows.

BRIEF DESCRIPTION OF THE DRAWINGS

FIGS. 1A and 1C show specific lysis from in vivo immunization and in vitro restimulation against each of the V3 B7 CTL epitope variants. BLCL=B lymphoblastoid cell (BCLC) no peptide coating control. C4=C4 Th determinant peptide on BCLC, V3MN, V3RF, V3EV91, and V3Can0A are the B7 CTL epitope variant peptide coated on BCLC. Data show patient in FIG. 1A responded to 1 of 4 B7 CTL epitope variants (the HTV EV91 variant) while the patient in FIG. 1C responded to 3 of 4 B7 epitope variants (HIV MN, EV91 and Can0A). FIGS. 1B and 1D show 2 HLA B7 negative individuals that made no CTL response to the B7-restricted CTL peptide immunogen after both in in vivo immunization and in vitro restimulation.

DETAILED DESCRIPTION OF THE INVENTION

Figure 1A:
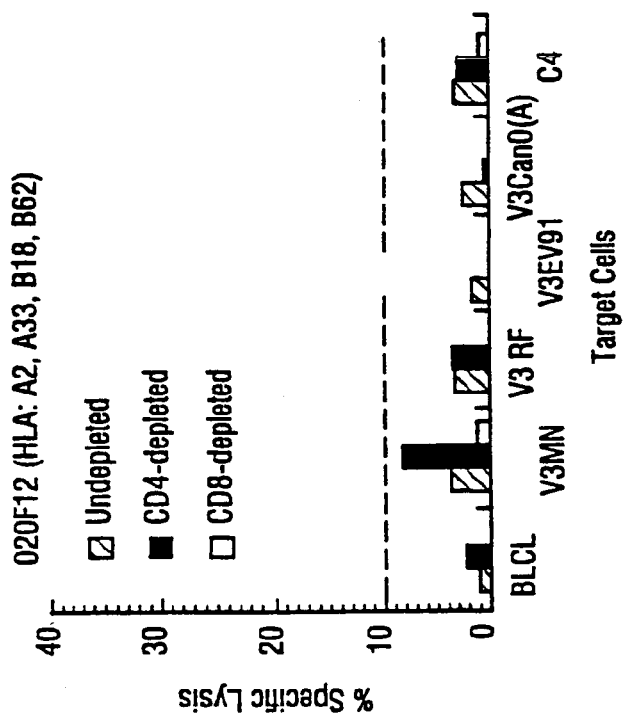
FIGS. 1A–1D. C4-V3 Th-CTL Peptides Induce HLA B7 Reactive CD8+ CTL in Normal HIV-1 Seronegative Humans.

The present invention relates to an HLA-based HIV vaccine. The invention further relates to a method of immunizing a patient against HIV by using such a vaccine.

The HLA-based vaccines of the invention can be designed based on available HLA databases. Results obtained in International Histocompatibility Testing Workshops, such as the most recent ones (Histocompatibility Testing 1980, Teresaki (Ed.), UCLA Tissue Typing Laboratory, Los Angeles, Calif. (1980), Histocompatibility Testing 1984, Albert et al (Eds.), Springer-Verlag, Berlin (1984), Immunobiology of HLA, 2 volumes, Dupont (Ed.), Springer-Verlag, New York, (1989), HLA 1991, 2 volumes, Tsuji et al (Eds.), Oxford University Press, Oxford (1992)), provide such a database.

The International Histocompatibility Workshop data (such as Histocompatibility Testing 1984, Albert et al (Eds.), Springer-Verlag, Berlin (1984), HLA 1991, 2 volumes, Tsuji et al (Eds.), Oxford University Press, Oxford (1992)), supplemented with published data from selected laboratories (such as Williams et al, Human Immunol. 33:39–46 (1992), Chandanayingyong et al, In Proceedings of the Second Asia and Oceania Histocompatibility Workshop Conference, Simons et al (Eds.), Immunopublishing, Toorak, pgs. 276–287 (1983)) provide an estimate of the frequencies of HLA alleles that have been shown to serve as restriction elements for HIV CTL epitopes (HIV Molecular Immunology Database (1995), Korber et al (Eds.), Los Alamos National Laboratory: Published by Theoretical Biology and Biophysics Group, Los Alamos National Laboratory, Los Alamos, N. Mex. 87545). Table 1 summarizes these frequencies for the four populations: African Americans, North American Indians, USA Caucasians, and Thais, used here for purposes of exemplification. Section II of the Los Alamos HIV epitope database of Korber et al (HIV Molecular Immunology Database (1995), Los Alamos National Laboratory: Published by Theoretical Biology and Biophysics Group, Los Alamos National Laboratory, Los Alamos, N. Mex. 87545) lists the CTL epitopes by HLA restriction element. Using these two sets of data and the Hardy-Weinberg theorem (Hardy, Science 28:49–50 (1908)), the proportion of each of the four populations that would be predicted to present peptides to the immune system if a limited number of HIV epitopes were included in a vaccine designed specifically for that population can be estimated. A similar calculation for a vaccine designed to be immunogenic for all four populations has been made. These results are presented in Table 2.

The strategy that can be used in this analysis is to first identify the most frequent restriction elements in the population under consideration for vaccination (or common to the 4 populations), to identify peptides that are presented by more than one HLA allele, and then to seek commonality between these two lists. Probability calculations then utilize the frequencies of the commonality alleles supplemented by those of additional high frequency alleles in the population. Alleles can be added until the proportion of the individuals in the population carrying one or more of the alleles in the list is at an acceptable level, for instance, greater than 90% in the examples. The aim is to maximize the sum of the HLA gene frequencies that recognize the least number of different HIV peptides to be included in an HIV immunogen. The next step is to choose the peptides associated with the restricting allele. In some instances, only one peptide is associated with an allele while in others, multiple peptides are presented by the same allele.

Criteria that can be used choosing which immunogenic epitopes to be included in a preventive HIV immunogen are listed below:

1. Peptides reported to be immunogenic in situations thought to reflect protection from retroviral infection or protection from retroviral-induced immunodeficiency disease (ie, in non-progressors to AIDS).

2. Peptides presented to the immune system by HLA restricting elements reported to be associated with non progression to AIDS (for example, Haynes et al, Science 171:324–328 (1996)).

3. Peptides reported to be "immunodominant" stimulators of HLA class I-restricted anti-HIV CTL responses (Nowak et al, Nature 375:606–611 (1995)).

4. Peptides reported presented by several disparate HLA class I allotypes.

For the four population cohorts considered in detail here by way of example, as few as 2 and as many as 5 epitopes are required to achieve a theoretical protection level of at least 90% (Table 2). The different numbers of required epitopes reflect the relative amounts of HLA Class I polymorphism observed in the different ethnic groups and presentation of a peptide by multiple HLA class I molecules. To date, HIV peptides have been associated only with HLA restriction elements that are infrequent in some populations. As more data are accumulated for other epitopes, some that are associated with higher frequency restriction elements may be identified.

A comparison between the individual and combined populations (Table 2) demonstrates that relatively little is gained by including epitopes that are associated with low frequency alleles. The proportion of individuals protected approaches 100% asymptotically so that even adding on epitopes associated with high frequency alleles adds little to the proportion as this level is approached. This is illustrated by the North American Indians where including 6 more epitopes associated with 5 very low frequency alleles and one intermediate frequency allele in the combined theoretical vaccine adds only 3.0% protection.

U.S. Pat. No. 5,993,819 (the contents of which is incorporated herein by reference) also includes a description of the steps involved in the development of an HLA-based HIV vaccine. In Table XXVI of that patent, the following vaccine formula is provided which is equally applicable here:

$$Th_1\text{-}X_1,\ Th_2\text{-}X_2,\ Th_3\text{-}X_3,\ \ldots\ Th_N\text{-}X_N$$

where Th=immunodominant T helper epitopes and X=MHC Class I CTL epitopes. In the context of a preferred embodiment of the invention, Table 3 provides specific TH-X peptides (see vaccines 6, 8 and 10, particularly vaccines 6 and 8) that can be admixed, formulated with a pharmaceutically acceptable carrier, and adjuvant, as appropriate, and administered to a patient in order to effect immunization. The optimum amount of each peptide to be included in the vaccine and the optimum dosing regimen can be determined by one skilled in the art without undue experimentation.

As an alternative to using mixtures of individual Th-X peptides, the vaccine of the presently preferred embodiment can also take the form of a linear array of Th-X epitopes (see the linear arrays of MVA 6–10 in Table 4, particularly MVA 6 and MVA 8), preferably, expressed in a modified *Vaccinia ankara* (Zentralbl. Bakterial 167:375–390 (1978); Nature Med. 4:397–402 (1988)) or other live vector such as an adenoviral vector or a canary pox vector (Weinhold et al, Proc. Natl. Acad. Sci. 94:1396–1401 (1997)). Upon expression with HIV gag p55, pseudovirons (particles) are produced (see, for example, the linear arrays of MVA 7 and 9 in Table 4). Standard procedures can be used to formulate the vaccine (e.g., with a carrier and, as appropriate, with an adjuvant) and optimum dosing regimes can be determined by one skilled in the art without undue experimentation.

In a further embodiment, the vaccine of the present invention includes MHC Class I restricted cytotoxic T lymphocytes (CTL) epitopes from HIV p17 and p24 gag regions. Known HIV CTL epitopes and their MHC restricting elements are listed in "HIV Molecular Immunology Database, 1999" (Korber, BTM, Brander, C., Haynes, B. F. et al Editors, Published by the Theoretical Biology and Biophysics Group T-10, Mail Stop K710 Los Alamos National Laboratory, Los Alamos, N. Mex. 87545). The CTL regions designated CTL-J, CTL-K, CTL-L and CTL-M are selected for Vaccine 11 in Table 3. The full peptide has been designed to have at the N-terminus of the epitope the optimal Th determinant, ThA E9V from HIV gp120 C4 region. The restricting elements predicted to respond to these peptides are listed to the right in Table 3. Thus, a practical HIV gag CTL immunogen is set forth in Table 6, with A-Th/A-CTL and B-Th/B-CTL peptides mixed with the peptides in Vaccine 11. The 25 HLA Class I molecules predicted to recognize the peptides in the mixture of peptides in Table 6 are listed at the bottom of the table.

Complex immunogens made up of CTL sequences, for example, from the Los Alamos Database (Korber, BTM, Brander, C., Haynes, B. F. et al Editors, Published by the Theoretical Biology and Biophysics Group T-10, Mail Stop K710 Los Alamos National Laboratory, Los Alamos, N. Mex. 87545) can be prepared by adding to the sequences in Table 6, new sequences from CTL epitopes in envelop, rev, nef, tat, pol and other regions of the HIV genome. These sequences can be formulated with T helper sequences as above in Table 6 (generic Th-X1, Th-X2 . . . Th-Xn), or can be delivered in shorter sequences of X1,X2, . . . Xn, with T cell help being delivered by an appropriate adjuvant. In these generic designs, Th represents a helper T cell epitope, and X represents a HLA Class I restricted CTL epitope.

At each CTL sequence, there are many variants that can be included in the peptide mix in the above vaccine designs, in order to provide CTL that attack a sufficient number of HIV variants to prevent infection or to control infection. Variants are listed for each HIV Clade in the Los Alamos database for HIV sequences, "Human Retroviruses and AIDS", Kuiken, C, Foley, B et al Editors, Published by the Theoretical Biology and Biophysics Group T-10, Mail Stop K710 Los Alamos National Laboratory, Los Alamos, N. Mex. 87545.

Since different geographic locations around the world have different HIV Clades infecting patient cohorts, the above peptide design can be modified to be appropriate for the Clade or Clades of HIV that are relevant for a particular geographic region. For example, the Los Alamos Database of HIV Sequences has a listing of sequences by country and by clade. Therefore, to design a CTL vaccine for Zambia in Sub-saharan Africa, the principles and general CTL epitope design described as above can be employed but using the most common or consensus sequences of the Clades and isolates in the data base from Zambia. This general strategy applyies to design of CTL immunogens for any geographic region of the world.

Peptides have the greatest use in focusing the immune response on many dominant and subdominant CTL epitopes of HIV, but may benefit from a prime from another type of immunogen. Thus, the sequences described above and given in Tables 3 and 6, as well as Zambian sequences and or sequences of epitopes from rev, nef, tat, pol or env, can also be constructed in linear arrays of CTL epitopes with or without T helper determinants, for example, in either plasmid DNA constructs or in live vector constructs such as Modified Vaccinia Ankara or in mycobacteria tuberculosis strains that are attenuated, such as BCG (Jacobs et al, Nature Medicine 2:334 (1996)). These DNA or live vectors with linear arrays of CTL epitopes can be used as either primes or boosts of peptides or of each other to optimally give CTL anti-HIV responses.

It will be appreciated that this embodiment of the invention includes not only the specific Th-X peptides, and derivatives thereof (e.g. as shown in MVA 7 and MVA 9 in Table 4), shown, for example, in Tables 3 and 4, but also includes variants of the indicated peptides as well, particularly variants of the CTL epitopes shown. The mixture or linear array of Th-x peptides can be used alone or as one component of a multi-component vaccine. It will also be appreciated that the peptides of the invention can be synthesized using standard techniques. It will also be appreciated that the vaccine of the present invention can take the form of a DNA vaccine the expression of which in vivo results in the expression of the peptides, or linear arrays of same, described above.

Suitable routes of administration of the present vaccine include systemic (e.g. intramuscular or subcutaneous). Alternative routes can be used when an immune response is sought in a mucosal immune system (e.g., intranasal). Appropriate routes and modes of administration can be selected depending, for example, on whether the vaccine is a peptide or DNA vaccine or combination thereof.

Certain aspects of the present invention are described in greater detail in the Example that follows.

EXAMPLE 1

Studies of Th-CTL Mutivalent in HLA B7+ Humans

Immunogenicity and Safety of the C4-V3 Th-CTL Polyvalent Immunogen in HIV Seropositive Patients with CD4+ T Cell Counts >500/mm3 (DATRI010). The DATRI010 human trial of the C4-V3 PV immunogen has been completed (Bartlett et al, AIDS Res. Hum. Retro. 12:1291–1300 (1998)). The immunogen was 4 Th-CTL peptides with the Th epitope the same in each peptide and the CTL peptide was four variants of a B7-restricted env CTL epitope (Haynes, Res. Human Retro. 11:211–221 (1995), Beddows et al, J. Gen. Virol. 79:77–82 (1998), Table 5). Ten HIV-infected, HLA B7-positive patients with CD4+ T cells >500/mm3 were enrolled. Eight patients received 2 mg of C4-V3 polyvalent immunogen (ie, 500 µg of each peptide) emulsified in incomplete Freund's adjuvant (Seppic ISA51) IM X5 over 24 weeks, and 2 controls received ISA51 IM alone. Vaccine recipients had excellent boosts of Th proliferative levels and neutralizing antibody levels to TCLA HIV (Bartlett et al, AIDS Res. Hum. Retro. 12:1291–1300 (1998)). However, in the setting of HIV infection, PBMC suspensions of immunized B7+ subjects had minimal direct CTL activity to the B7-restricted env CTL epitope in the immunogen to peptide coated targets or to vaccinia infected targets (i.e. the B7 gp120 CTL epitope was non-dominant in the setting of HIV infection) (Bartlett et al, AIDS Res. Hum. Retro. 12:1291–1300 (1998)).

AVEG020 Trial of Th-CTL C4-V3 Peptides in Seronegative Subjects. In conjunction with NIAID, DAIDS, DATRI and WLVP, AVEG020 "Phase 1 Safety and Immunogenicity Trial of C4-V3 Peptide Immunogen in HIV Seronegative Subjects" was carried out at Vanderbilt, Rochester, and Seattle as a multicenter trial (AVEG020 Doses: High Dose=4 mg total dose, 1 mg of each peptide per dose; Low Dose=1 mg total dose, 250 µg of each peptide per dose).

Figure 1B:
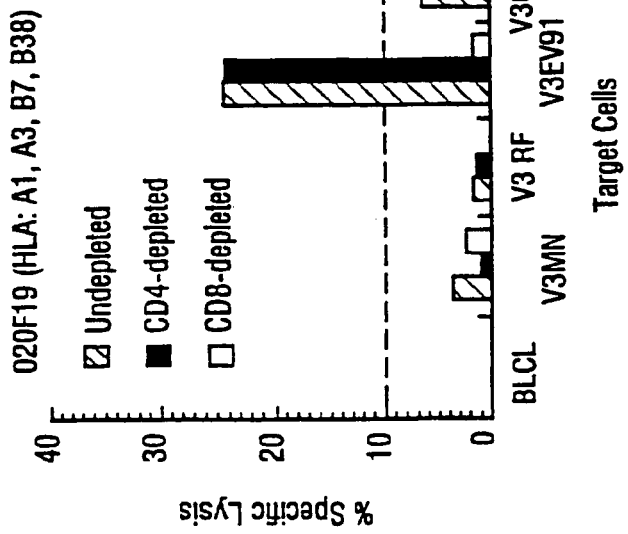
Figure 1D:
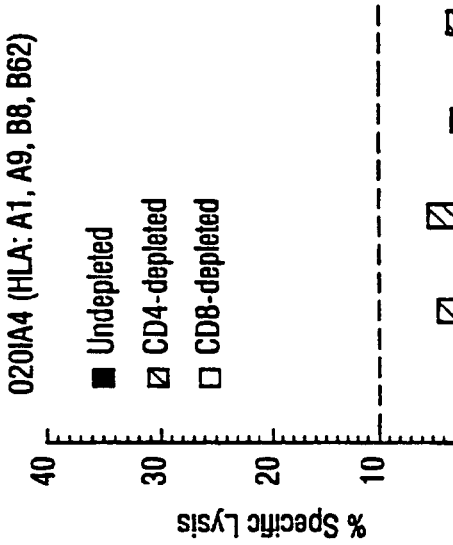
Figure 1C:
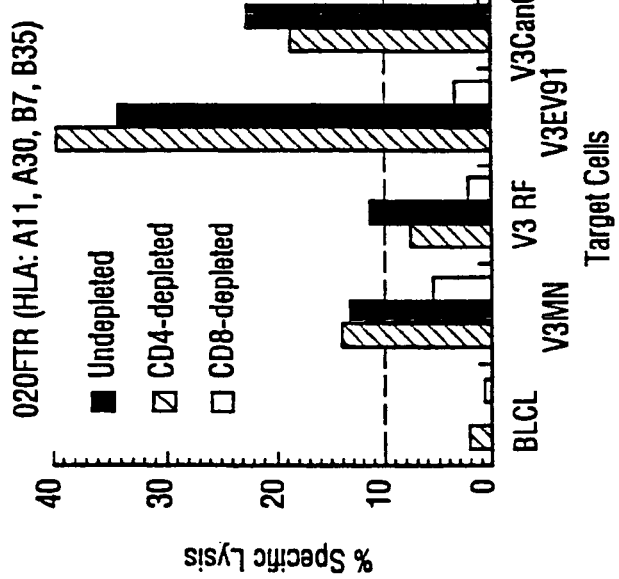

Studies were made of 13 subjects (9, B7– and 4 B7+) after two immunizations 250 µg of each peptide variant. Of 9 HLA B7-subjects, 0/9 had PB CTL activity to any of the peptide variants of the B7-restricted gp120 env CTL epitope in the immunogen (FIGS. 1B and 1D). In contrast, 2/4 HLA B7+ subjects had high levels of CTL activity to the B7 epitope that was mediated by CD8+ T cells and was MHC restricted after only two immunizations (FIGS. 1A and 1C). These data provided direct evidence that Th-CTL immunogens, when formulated in potent adjuvants, could induce MHC Class I-restricted CATL in humans. Whereas one subject responded to one of the 4 B7 epitope variants, the other subject (FIG. 1A) responded to 3 of the 4 CTL variants. These data demonstrated that a human host could respond to more than one CTL epitope variant in an immunogen, and indicated that epitope-based immunizations could be used to induce MHC Class I-restricted CD8+ CTL responses to CTL epitopes and to their variants.

All documents cited above are hereby incorporated in their entirety by reference.

One skilled in the art will appreciate from a reading of this disclosure that various changes in form and detail can be made without departing from the true scope of the invention.

TABLE 1

Frequencies of HLA Class I Allels That an Known to Serve as HIV CTL Restriction Elements in Four Populations

| HLA Alleles | Fequencies* | | | |
| --- | --- | --- | --- | --- |
| | Afican Americans | USA Caucasians | North American Indians | Thais |
| A2 | 16.7 | 28.3 | 25.5 | 25.5 |
| A3 | 8.9 | 12.2 | 2.9 | 1.5 |
| A11 | 2.3 | 5.5 | 1.0 | 32.5 |
| A24 | 4.7 | 9.6 | 19.6 | 14.6 |
| A28 | 10.9 | 4.5 | 6.9 | 0.8 |
| A30 | 9.5 | 2.6 | 2.0 | 1.1 |
| A31 | 1.7 | 2.0 | 27.5 | 1.7 |
| A32 | 1.0 | 5.1 | 2.0 | 0.2 |
| A33 | 8.1 | 1.0 | 1.0 | 13.6 |
| B7 | 8.3 | 10.0 | 3.9 | 2.7 |
| B8 | 3.2 | 10.0 | 5.6 | 0.2 |
| B12 (44) | 6.2 | 10.4 | 3.9 | 5.4 |
| B13 | 0.9 | 3.0 | 1.0 | 9.3 |
| B14 | 3.0 | 4.1 | 2.9 | 0.4 |
| B17 | 10.9 | 4.9 | 1.0 | 8.1 |
| B18 | 3.3 | 4.9 | 1.0 | 2.5 |
| B27 | 1.6 | 4.1 | 2.9 | 6.0 |
| B35 | 7.7 | 8.5 | 18.6 | 2.5 |
| B37 | 0.9 | 2.2 | 0.0 | 1.4 |
| B52 | 1.1 | 1.2 | 2.9 | 3.1 |
| B53 | 12.8 | 0.8 | 0.0 | 0.0 |
| B57 | 4.2 | 3.9 | 1.0 | 5.2 |
| B60 | 1.3 | 4.5 | 2.9 | 8.3 |
| B62 | 1.4 | 5.5 | 4.9 | 5.0 |
| Cw3 | 9.6 | 12.6 | 22.4 | 15 |
| Cw4 | 21.0 | 9.8 | 15.4 | 6 |

*Frequencies for HLA-A and HLA-B alleles are taken from HLA 1991 [21]. HLA-C for African Americans and USA Caucasians are taken from Histocompatibility Testing 1984 [19]. HLA-C for North American Indians from Williams and McAuley, 1992 [22], and HLA-C for This from the Proceedings of the Second Asia and Oceania Histocompatibility Workshop Conference [23].

TABLE 2

Proportion of each of the four populations that would be predicted to present peptides to the immune system

| Population | HLA Restriction Elements chosen | HIV Protein | Epitope Location | Epitope |
|---|---|---|---|---|
| a) African Americans | A2, A3, A11, B35 | nef | 73–82 | QVPLRPMTYK |
| | A28, B14 | gp41 | 583–592 | VERYLKDQQL |
| | A30, B8 | gp41 | 844–863 | RBIRQGLERALL |
| | B17, B37 | nef | 117–128 | TQGYFPQWQUYT |
| | Cw4 | gp120 | 576–383 | (S)FNCGGEFF |

(Proportion of African Americans expected to present these 5 epitopes is 92.3%)

| | | | | |
|---|---|---|---|---|
| b) USA Caucasians | A2, A3, A11, B35 | nef | 73–82 | QVPLRPMTYK |
| | A30, B8 | gp41 | 844–863 | RRIRQGLERALL |
| | B7 | gp120 | 302–312* | RPNNNTRKSI |
| | | nef | 126–138* | NYTPGPGVRYPLT |
| | B12 | p24 | 169–184 | IPMFSALSEGATPQDL |

(Proportion of USA Caucasians expected to present these 4 epitopes is 90.2%)

| | | | | |
|---|---|---|---|---|
| c) North American Indians | A2, A3, A11, B35 | nef | 73–82 | QVPLRPMTYK |
| | A24 | gp41 | 584–591* | YLKDQQL |
| | | nef | 120–144* | YFPDWQNYTPGPGIRYPLTFGWCYK |
| | A31 | gp41 | 770–780 | RLRDLLLIVTR |

(Proportion of North American Indians expected to present these 3 epitopes is 96.4%)

| | | | | |
|---|---|---|---|---|
| d) Thais | A2, A3, A11, B35 | nef | 73–82 | QVLRPMTYK |
| | A24 | gp41 | 584–591* | YLKDQQL |
| | | nef | 120–144* | YFPDWQNYTPGPGIRYPLTFGWCYK |

(Proportion of Thais expected to present these 2 epitopes is 93.6%)

| | | | | |
|---|---|---|---|---|
| e) African Americans USA Caucasians North American Indians Thais | A2, A3, A11, B35 | nef | 73–82 | QVPLRPMTYK |
| | A28, B14 | gp41 | 583–592 | VERYLKDQQL |
| | A30, B8 | gp41 | 844–863 | RRIRQGLERALL |
| | B17, B37 | nef | 117–128 | TQGYFPQWQNYT |
| | Cw4 | gp120 | 376–383 | (S)FNCGGEFF |
| | B7 | gp120 | 302–312* | RPNNNTRKSI |
| | | nef | 126–138* | NYTPGPGVRYPLT |
| | B12 | p24 | 169–184 | IPMFSALSEGATPQDL |
| | A31 | gp41 | 770–780 | RLRDLLLIVTR |
| | A24 | gp41 | 584–591* | YLKDQQL |
| | | nef | 120–144* | YFPDWQNYTPGPGIRYPLTFGWCYK |

(Proportions of African Americans, USA Caucasians, North American Indians, and Thais expected to present these 9 epitopes are 95.4%, 97.5%, 99.4%, and 97.2%, respectively)

*The criteria upon which choices among peptides should be made are not yet known. It may be important to choose peptides that have been reported to be immunogenic in non-progressors to AIDS or that have been reported to induce immunodominant anti-HIV T-cell responses.

The epitopes listed above correspond to the following sequence identifiers, respectively: SEQ ID NOs:1–5, SEQ ID NO:1, SEQ ID NO:3, SEQ ID NOs:6–8, SEQ ID NO:1, SEQ ID NOs: 9–12, SEQ ID NO:9, SEQ ID NOs:1—8, SEQ ID NO:11, SEQ ID NO:9, and SEQ ID NO:13.

TABLE 3

Th-CTL Peptide Prototype Vaccine Immunogens for Testing in Either Mice, Rhesus Macaque of Human

| Vaccine number | Name of Peptides | Species in which o be studied | Amino acid sequence | Restricting elements for CTL epitope |
|---|---|---|---|---|
| 1. | Mouse HIV-1 Th-CTL epitopes | | Th    -    CTL | |
| | A-Th/A-CTL | Mouse | HAGPIAPGQMREPRG-KQIINMWQEVGKAMYA | H-2$^{mid}$ |
| | B-Th/B-CTL | Mouse | KEKVYLAWVPAHKGIG-MYAPPIGGQI | H-2 K$^4$ |
| | C-Th/C-CTL | Mouse | QLLFIHFRIGCRHSR-DRVIEVVQGAYRAIR | H-2$^{same}$(D$^4$) |
| | D-Th/D-CTL | Mouse | EQMHEDIISLWDQSL-RIHIGPGRAFYTTKN | H-2 D$^4$ |
| 3. | Macaque SIV/HIV-1 Th-CTl epitopes | | Th    -    CTL | |
| | Th1/CTL/SIV Gag | Macaque | ELYKYKVVKIEPLGVAPTKA-CTPYDINQM | Mamu-A *01 |
| | Th2/CTL/SIV Pol | Macaque | VSTVQCTHGIRPVVSTQLLL-STPPLVRL | Mamu-A *01 |
| | Th3/CTL/HIV-1 Env | Macaque | STSIRGKVQKEYAFFYKLDI-YAPPISGQI | Mamu-A *01 |
| 5. | Macaque SIV/HIV-1 Th-CTL p11c epitopes variants | | Th    -    CTL | |
| | Th1/CTL/SIV Gag | Macaque | ELYKYKVVKIEPLGVAPTKA-CTPYDINQM | Mamu-A *01 |
| | Th2/CTL/SIV Gag/p11c/I-Y | Macaque | VSTVQCTHGIRPVVSTQLLL-CTPYDYNQML | Mamu-A *01 |
| | Th3/CTL/SIV Gag/p11c/I-A | Macaque | STSIRGKVQKEYAFFYKLDI-CTPYDANQML | Mamu-A *01 |
| | Th4/CTL/SIV Gag/p11c/I-D | Macaque | EYAFFYKLDIIPIDNDTTSY-CTPYDDNQML | Mamu-A *01 |
| | Th5/CTL/SIV Gag/p11c/I-K | Macaque | REQFGNNKTIIFKQSSGGDPE-CTPYDKNQML | Mamu-A *01 |
| 6. | Human HIV-1 Th-CTL overlapping epitopes | | Th    -    CTL | |
| | A-Th/A-CTL | Human | KQIINMWQEVGKAMYA-KAFSPEVIPMF | HLA B57.B68 |
| | B-Th/B-CTL | Human | YKRWIILGLNKIVRMYS-NPPIPVGEIYKRWI-ILGLNKIVRMYSPTSI | HLA B35.B8.B27.A33.Bw62.B52 |
| | C-Th/C-CTL | Human | DRVIEVVQGAYRAIR-VGFPVRPQVPLRPMTYK | HLA A1.B7.B8.B35.A11.A2.A3.A31 |
| | D-Th/D-CTL | Human | ASLWNWFNITNWLWY-WVYHTQGFFPDWQNYTP | HLA B7.B57.A1.B8.B18.B35 |
| 8. | Human HIV-1 Th-dominant/subdominant CTL epitopes | | Th    -    CTL | |
| | A-Th/E-CTL | Human | KQIINMWQEVGKAMYA-SLYNTVATL | HLA A2 |
| | B-Th/F-CTL | Human | YKRWIILGLNKIVRMYS-KIRLRPGGK | HLA A3 |
| | C-Th/G-CTL | Human | DRVIEVVQGAYRAIR-KRWIILGLNK | HLA B27 |
| | D-Th/H-CTL | Human | ASLWNWFNITNWLWY-GGKKKYKL | HLA B8 |
| | E-Th/I-CTL | Human | MREPRGSKIAGTTST-ERYLKDQQL | HLA B14 |
| 10. | Human HIV-1 Th-CTL p17 epitope (A2 Variants) | | Th    -    CTL | |
| | B-Th/E-CTL | Human | YKRWIILGLNKIVRMYS-SLYNTVATL | HLA A2 |
| | C-Th/J-CTL | Human | DRVIEVVQGAYRAIR-SLFNTVATL | HLA A2 |
| | A-Th/K-CTL | Human | QIINMWQEVGKAMYA-SLYNAVATL | HLA A2 |
| | D-Th/L-CTL | Human | ASLWNWFNITNWLWY-SLYNTVAVL | HLA A2 |
| | E-Th/M-CTL | Human | MREPRGSKIAGTTST-SLFNLLAVL | HLA A2 |

| Vaccine number | Name of Peptides | Amino acid sequence | Restricting elements for CTL epitope |
|---|---|---|---|
| 11. | Human HIV-1 Th-CTL overlapping epitopes | Th    -    CTL | |
| | A*-Th/J-CTL | KQIINMWQVVGKAMYA-GQMVHQAISPRTLNAWVKVV | A2.A202.A5.B7,B14.B57.B5701.B5801.B02.Cw3 |
| | A*-Th/K-CTL | KQIINMWQVVGKAMYA-ATPQDLNTMLNTVGGHQAAMQMLKETINEEAAEW | A2.A25.A26.B7.B12.B14.B1402.B27.B39.B52.B53.B57.B58.B8101.Cw8.Cw0102 |
| | A*-Th/L-CTL | KQIINMWQVVGKAMYA-GPKEPFRDYVDRFYKTLRAEQASQEVKNWMT | A2.A202.A5.A24.A2402.A25.A26.A33.B7.B8.B12.B14B35.B39.B44.B52.B53Bw62.B27.B2705.B57.B5701.B70.B71.Bw62.Cw3.Cw8.Cw0401 |
| | A*-Th/M-CTL | KQIINMWQVVGKAMYA-KIRLRPGGKKKYKLKHIVWGSEELRSLYNTVATLYCVHQRI | A1.A2.A3.A3.1.A03.A11.A23.A24.A0201.A2402.B8.B27.B42.B62.Bw62.Cw4 |

A*-Th = C4E9V

The amino acid sequences listed above correspond to the following sequence identifiers, respectively: SEQ ID NOs: 14–20, SEQ ID NO:18, and SEQ ID NOs:21–42.

TABLE 4

Linear Array of Th-CTL Epitopes To Be Expressed in Modified Vaccinia Ankara

MVA-1) HIV-1 mouse Th-CTL epitopes in

| A-Th/p24/(H-2 $^b$) | A-CTL/gp120(H-2 $^{abf}$) | B-Th/RT (H2 $^{dtk}$) | B-CTL/gp120(H-2K $^d$) |

HAGPIAPGQMREPRG--KQIINMWQEVGKAMYA----KEKVYLAWVPAHKGIG----MYAPPIGGQI-

| C-Th/vpr(H-2 $^d$) | C-CTL/gp41 (H-2 $^{dpuq}$) (D$^d$) | D-Th/gp120(H-2 $^d$) | D-CTL/gp120/(H-2D $^d$) |

--QLLFIHFRIGCRHSR---DRVIEVVQGAYRAIR----EQMHEDIISLWDQSL---RIHIGPGRAFYTTKN

MVA-2) p55/gag + the same HIV-1 mouse Th-CTL epitopes in MVA-1
MVA-3) HIV-1/SIV Th-CTL epitopes in

| Th1/gp120/DRB*w201 | CTL/SIV Gag (Mamu-A*01) | Th2/gp120/DRBI*5406 | CTL/SIV Pol (Mamu-A*01) |

ELYKYKVVKIEPLGVAPTKA-------CTPYDINQM--------VSTVQCTHGIRPVVSTQLLL-----STPPLVRL-

| Th3/gp120 | CTL/HIV-1 Env (Mamu-A*01) |

--STSIRGKVQKEYAFFYKLDI--------YAPPISGQI

MVA-4) p55/gag + the same HIV-1/SIV Th-CTL epitopes in MVA-3
MVA-5) SIV Th-CTL p11c epitope variants in

| Th1/DRB*w201 | CTL/SIV Gag (Mamu-A*01) | Th2/DRBI*5406 | CTL/Gag/p11c/I-Y |

ELYKYKVVKIEPLGVAPTKA----CTPYDINQML-------VSTVQCTHGIRPVVSTQLLL----CTPYDYNQML-

| Th3/P14 | CTL/Gag/p11c/I-A | Th4/P15 | CTL/Gag/pile/I-D |

-STSIRGKVQKEYAFFYKLDI---CTPYDANQML------EYAFFYKLDIIPIDNDTTSY------CTPYDDNQML-

| Th5/P33 | CTL/Gag/p11c/I-K |

-REQFGNNKTIIFKQSSGGDPE----CTPYDKNQML

MVA-6) HIV-1 human Th-CTL overlapping epitopes in

| A-Th/gp120//422-437 | A-CTL/p24/30–40 | B-Th/GTH1/130–146 | B-CTL/P24/121–150 |

KQIINMWQEVGKAMYA----KAFSPEVIPMF----YKRWIILGLNKIVRMYS----NPPIPVGEIYKRWIILGLNKIVRMYSPTSI-

| C-Th/gp41/317–331 | C-CTL/Nef/64–80 | D-Th/gp41/157–171 | D-CTL/Nef/111–127 |

--DRVIEVVQGAYRAIR---VGFPVRPQVPLRPMTYK---ASLWNWFNITNWLWY----WVYHTQGFFPDWQNYTP

Restricting elements tor CTL epitopes:

A-CTL epitope = HLA B57/B58: B-CTL epitopes = HLA B35/B8/B27/A33/Bw62/B52:
C-CTL epitope = HLA A1//B7/B8/B35/A11/A2/A3/A31); D-CTL epitope = HLA B7/B57/A1/B8/B18/B35.
MVA-7) p55 gag + the same HIV-1 human Th-CTL overlapping epitopes in MVA-6
MVA-8) HIV-1 Thdominant/subdominant CTL epitopes in

| A-Th/C4/422–437 | E-CTR/p17/77–85(A2) | B-Th/GTH1/130–146 | F-CTL/p17/18–26(A3) | C-Th/gp41/317–331 |

KQIINMWQEVGKAMYA-----SLYNTVATL-----YKRWIILGLNKIVRMYS----KIRLRPGGK------DRVIEVVQGAYRAIR-

| G-CTLp24/131–140(B27) | D-Th/gp41/157–171 | H-CTLp17/24–31(B8) | E-Th/p24/96–110 | I-CTLgp41/74–82(B14) |

--KRWIILGLNK-----ASLWNWFNITNWLWY-----GGKKKYKL------MREPRGSKIAGTTST----ERYLKDQQL-

MVA-9) p55/gag + the same HIV-1 Th-dominant/subdominant CTL epitopes in MVA-8
MVA-10) HIV-1 Th-CTL A2 p17 epitope (A2 Variants) in

| B-Th/GTH1/130–146 | E-CTR/p17/77–85(A2) | C-Th/gp41/317–331 | J-CTL/P17/Consensus A | A-Th/C4/422–437 |

YKRWIILGLNKIVRMYS----SLYNTVATL------DRVIEVVQGAYRAIR----SLFNTVATL-------KQIINMWQEVGKAMYA-

| K-CTL/P17/RF | D-Th/gp41/157–171 | L-CTL/P17/Consensus F | E-Th/p24/96–110 | M-CTL/P17/V1525 |

--SLYNAVATL----ASLWNWFNITNWLWY-------SLYNTVAVL--------MREPRGSKIAGTTST-----SLFNLLAVL

The epitopes presented above correspond to the following sequence identifiers, respectively: SEQ ID NOs:43–94.

TABLE 5

HIV Polyvalent C4-V3 Peptides Studied in Guinea Pigs, Primates Or In Humans

| Peptide | gp120 C4 Region gp120 V3 Region |
|---|---|
| C4-V3MN | KQIINMWQEVGKAMYATRPNYNKRKRIHIGPGRAFYTTK |
| C4-V3RF | KQIINMWQEVGKAMYATRPNNNTRKSITKGPGRVIYATG |
| C4-V3EV91 | KQIINMWQEVGKAMYATRPGNNTRKSIPIGPGRAFIATS |
| C4-V3CanOA | KQIINMWQEVGKAMYATRPHNNTRKSIHMGPGKAFYTTG |
| C4E9G-V3RF | KQIINMWQGVGKAMYATRPNNNTRKSITKGPGRVIYATG |

TABLE 5-continued

HIV Polyvalent C4-V3 Peptides Studied in Guinea Pigs, Primates Or In Humans

| Peptide | gp120 C4 Region gp120 V3 Region |
|---|---|
| C4E9V-V3RF | KQIINMWQVVGKAMYATRPNNNTRKSITKGPGRVIYATG |
| C4K12E-V3RF | KQIINMWQEVGEAMYATRPNNNTRKSITKGPGRVIYATG |

Sequences from the Los Alamos Database.

The peptides presented above correspond to the following sequence identifiers, respectively: SEQ ID NOs:95–101.

TABLE 6

Th-CTL Peptide Prototype Vaccine Immunogens derived from HIV-1 gag

| Vaccine number | Name of Peptides | Amino acid sequence | Restricting elements for CTL epitope |
|---|---|---|---|
| | Human HIV-1 Th-CTL overlapping epitopes | Th-CTL | |
| 6 | A-Th/A-CTL | KQIINMWQEVGKAMYA-KAFSPEVIPMF | B57,B58 |
| 6 | B-Th/B-CTL | YKRWIILGLNKIVRMYS-NPPIPVGEIYKRWIILGLNKIVRMYSPTSI | B35,B8,B27,A33,Bw62,B52 |
| 11 | A*-Th/J-CTL | KQIINMWQVVGKAMYA-GQMVHQAISPRTLNAWVKVV | A2,A202,A5,B7,B14,B57,B5701, B5801,B02,Cw3 |
| 11 | A*-Th/K-CTL | KQIINMWQVVGKAMYA-ATPQDLNTMLNTVGGHQAAMQMLKETINEEAAEW | A2,A25,A26,B7,B12,B14,B1402, B27,B39,B52,B53,B57,B58,B8101, Cw8,Cw0102 |
| 11 | A*-Th/L-CTL | KQIINMWQVVGKAMYA-GPKEPFRDYVDRFYKTLRAEQASQEVKNWMT | A2,A202,A5,A24,A2402,A25,A26,A33, B7,B8,B12,B14,B35,B39,B44,B52, B53,Bw62,B27,B2705,B57,B5701, B70,B71,Bw62,Cw3,Cw8,Cw0401 |
| 11 | A*-Th/M-CTL | KQIINMWQVVGKAMYA-KIRLRPGGKKKYKLKHIVWGSEEL-RSLYNTVATLYCVHQRI | A1,A2,A3,A3.1,A03,A11,A23,A24, A0201,A2402,B8,B27,B42,B62, Bw62,Cw4 |

A*-Th = C4E9V
Summary of restracting elements for CTL epitopes in Vaccines A, B, J, K, L and M
A: A1, A2(02), (01), A3, A3.1, A5, A11, A23, A24(02), A25, A26 and A33.
B: B7, B8, B12, B14(02), B27(05), B35, B39, B42, B44, B52, B53, B57(01), B58(01), B62(w62), B70 and B71.
C: Cw3, Cw4, Cw0401 and Cw8.

The amino acid sequences above correspond to the following sequence identifiers, respectively: SEQ ID NOs: 102–107.

What is claimed is:

1. An immunogenic composition comprising the peptide of SEQ ID NO:26.

2. A method of inducing an immune response in a patient comprising administering to said patient an amount of the immunogenic composition according to claim 1 sufficient to effect said induction.

3. The immunogenic composition according to claim 1, wherein said immunogenic composition further comprises a carrier.

4. The immunogenic composition according to claim 1, wherein said immunogenic composition further comprises at least one peptide selected from the group consisting of the peptides of SEQ ID NOs:14–25 and 27–42.

5. A method of inducing an immune response in a patient comprising administering to said patient an amount of the immunogenic composition according to claim 4 sufficient to effect said induction.

* * * * *